(12) United States Patent
Garcia Sabido et al.

(10) Patent No.: US 12,727,899 B2
(45) Date of Patent: Sep. 8, 2026

(54) INTRAVASCULAR DEVICE WITH AN IMPROVED ATTACHMENT OF ITS ELEMENTS AND A METHOD OF MANUFACTURING THEREOF

(71) Applicant: ANACONDA BIOMED, S.L., Sant Quirze del Vallès (ES)

(72) Inventors: Daniel Garcia Sabido, Vilafranca del Penedès (ES); Aina Laguarta Alapont, Manresa (ES); Iñaki Galve Murillo, Barcelona (ES); Ofir Arad Hadar, Sant Cugat del Vallès (ES); Jordi Cardona Vidal, La Garriga (ES)

(73) Assignee: ANACONDA BIOMED, S.L., Sant Quirze del Vallès (ES)

( * ) Notice: Subject to any disclaimer, the term of this patent is extended or adjusted under 35 U.S.C. 154(b) by 44 days.

(21) Appl. No.: 18/722,470

(22) PCT Filed: Dec. 19, 2022

(86) PCT No.: PCT/EP2022/086675

§ 371 (c)(1),
(2) Date: Jun. 20, 2024

(87) PCT Pub. No.: WO2023/117919

PCT Pub. Date: Jun. 29, 2023

(65) Prior Publication Data

US 2025/0134540 A1 May 1, 2025

(30) Foreign Application Priority Data

Dec. 21, 2021 (EP) .................................... 21383177

(51) Int. Cl.
*A61B 17/221* (2006.01)
*A61B 17/00* (2006.01)

(52) U.S. Cl.
CPC ...... *A61B 17/221* (2013.01); *A61B 17/00234* (2013.01); *A61B 2017/00477* (2013.01);
(Continued)

(58) Field of Classification Search
CPC ........... A61M 25/001; A61M 25/0012; A61M 25/0067; A61M 25/0068; A61M 25/0069;
(Continued)

(56) References Cited

U.S. PATENT DOCUMENTS 4,574,176 A 3/1986 Sharp
4,794,231 A 12/1988 Banas et al.
(Continued)

FOREIGN PATENT DOCUMENTS

AU 2018274903 B2 4/2020
CN 102973332 A 3/2013
(Continued)

OTHER PUBLICATIONS

Ríos Garriga et al; U.S. Appl. No. 19/094,121 entitled "Delivery catheter device and system for accessing the intracranial vasculature," filed Mar. 28, 2025.
(Continued)

*Primary Examiner* — Kankindi Rwego
(74) *Attorney, Agent, or Firm* — Shay Glenn LLP

(57) ABSTRACT

An intravascular device with an improved attachment of its elements is provided. The intravascular device comprises a vascular pusher comprising a distal connection portion; a tool attached to, and extending from, the distal connection portion of the vascular pusher, the tool comprising a mesh of at least two sets of filaments and comprising a proximal connection portion having laser-cut proximal ends; and an attachment between the tool proximal connection portion and the vascular pusher distal connection portion adapted to keep the tool connected to the vascular pusher, the attach-
(Continued)

ment having an outer diameter substantially equal to an outer diameter of the vascular pusher. A method of manufacturing an intravascular device is also provided.

15 Claims, 15 Drawing Sheets

(52) U.S. Cl.
CPC ............... *A61B 2017/00526* (2013.01); *A61B 2017/00951* (2013.01); *A61B 2017/00955* (2013.01); *A61B 2017/2215* (2013.01)

(58) Field of Classification Search
CPC ... A61M 25/0074; A61M 39/10; A61B 17/34; A61B 17/3417; A61B 17/3421; A61B 2017/0047; A61B 2017/22079; A61B 2017/3454; A61B 1/0008; A61B 1/00087; A61B 1/00101; A61B 1/00105; A61B 1/0011; A61B 1/00112; A61B 1/00121; A61B 1/00128
USPC .......................................................... 606/127
See application file for complete search history.

(56) References Cited

U.S. PATENT DOCUMENTS 4,921,478 A 5/1990 Solano et al.
5,011,488 A 4/1991 Ginsburg
5,092,839 A 3/1992 Kipperman
5,102,415 A 4/1992 Guenther et al.
5,190,561 A 3/1993 Graber
5,234,416 A 8/1993 MacCaulay et al.
5,449,373 A 9/1995 Pinchasik et al.
5,603,705 A * 2/1997 Berg .................. A61M 25/005 604/527
5,605,530 A 2/1997 Fishell et al.
5,769,871 A 6/1998 Mers Kelly et al.
5,908,435 A 6/1999 Samuels
5,971,938 A 10/1999 Hart et al.
5,972,019 A 10/1999 Engelson et al.
6,066,149 A 5/2000 Samson et al.
6,159,230 A 12/2000 Samuels
6,190,303 B1 2/2001 Glenn et al.
6,402,771 B1 6/2002 Palmer et al.
6,514,273 B1 2/2003 Voss et al.
6,663,650 B2 12/2003 Sepetka et al.
6,695,858 B1 2/2004 Dubrul et al.
6,730,104 B1 5/2004 Sepetka et al.
6,752,819 B1 6/2004 Brady et al.
7,004,954 B1 2/2006 Voss et al.
7,108,677 B2 9/2006 Courtney et al.
7,578,830 B2 8/2009 Kusleika et al.
7,686,825 B2 3/2010 Hauser et al.
7,867,272 B2 1/2011 Niermann
7,993,302 B2 8/2011 Hebert et al.
8,088,140 B2 1/2012 Ferrera et al.
8,298,257 B2 10/2012 Sepetka et al.
8,679,142 B2 3/2014 Slee et al.
8,758,364 B2 6/2014 Eckhouse et al.
8,784,441 B2 7/2014 Rosenbluth et al.
8,858,497 B2 10/2014 Di Palma et al.
8,864,792 B2 10/2014 Eckhouse et al.
8,940,003 B2 1/2015 Slee et al.
8,984,003 B2 3/2015 Ahmed et al.
9,005,237 B2 4/2015 Eckhouse et al.
9,034,008 B2 5/2015 Eckhouse et al.
9,186,487 B2 11/2015 Dubrul et al.
9,463,035 B1 10/2016 Greenhalgh et al.
9,561,121 B2 2/2017 Sudin et al.
9,585,741 B2 3/2017 Ma
9,700,331 B2 7/2017 Grandfield et al.
9,844,381 B2 12/2017 Eckhouse et al.
9,861,783 B2 1/2018 Garrison et al.
10,285,720 B2 5/2019 Gilvarry et al.
10,292,804 B2 5/2019 Wang et al.
10,426,644 B2 10/2019 Shrivastava et al.
10,434,605 B2 10/2019 Feth et al.
11,013,523 B2 5/2021 Jacobi et al.
11,534,191 B2 12/2022 Ros Fabrega et al.
11,771,446 B2 10/2023 Salmon et al.
11,986,195 B2 5/2024 Cortinas Villazon et al.
2002/0049493 A1 4/2002 Jang
2003/0009150 A1* 1/2003 Pepin ................ A61M 25/0045 604/523
2003/0023299 A1 1/2003 Amplatz et al.
2003/0212430 A1 11/2003 Bose et al.
2003/0212439 A1 11/2003 Schuler et al.
2004/0024416 A1 2/2004 Yodfat et al.
2004/0073243 A1 4/2004 Sepetka et al.
2004/0098099 A1 5/2004 McCullagh et al.
2004/0143317 A1 7/2004 Stinson et al.
2004/0167565 A1 8/2004 Beulke et al.
2004/0199201 A1 10/2004 Kellett et al.
2004/0199243 A1* 10/2004 Yodfat ...................... A61F 2/01 623/1.15
2004/0243102 A1 12/2004 Berg et al.
2004/0260333 A1 12/2004 Dubrul et al.
2005/0209678 A1 9/2005 Henkes et al.
2006/0058838 A1 3/2006 Bose et al.
2006/0064073 A1 3/2006 Schonholz et al.
2006/0155305 A1 7/2006 Freudenthal et al.
2006/0293744 A1 12/2006 Peckham et al.
2007/0118165 A1 5/2007 DeMello et al.
2007/0188165 A1 8/2007 Kitanaka et al.
2007/0198028 A1 8/2007 Miloslavski et al.
2007/0203559 A1 8/2007 Freudenthal et al.
2007/0208367 A1 9/2007 Fiorella et al.
2007/0213765 A1 9/2007 Adams et al.
2007/0276332 A1 11/2007 Bierman
2007/0288038 A1 12/2007 Bimbo
2008/0228209 A1 9/2008 DeMello et al.
2008/0269774 A1 10/2008 Garcia et al.
2008/0269798 A1 10/2008 Ramzipoor et al.
2009/0163846 A1 6/2009 Aklog et al.
2009/0198269 A1 8/2009 Hannes et al.
2010/0004607 A1 1/2010 Wilson et al.
2010/0030256 A1 2/2010 Dubrul et al.
2010/0222864 A1 9/2010 Rivelli et al.
2011/0160763 A1 6/2011 Ferrera et al.
2011/0213297 A1 9/2011 Aklog et al.
2011/0213392 A1 9/2011 Aklog et al.
2012/0059309 A1 3/2012 Di Palma et al.
2012/0065660 A1 3/2012 Ferrera et al.
2012/0083868 A1 4/2012 Shrivastava et al.
2012/0114017 A1 5/2012 Bang et al.
2012/0116440 A1 5/2012 Leynov et al.
2012/0179181 A1 7/2012 Straub et al.
2012/0209311 A1 8/2012 Grandfield et al.
2012/0245671 A1 9/2012 Wainwright et al.
2013/0261638 A1 10/2013 Diamant et al.
2013/0325055 A1 12/2013 Eckhouse et al.
2013/0325056 A1 12/2013 Eckhouse et al.
2014/0052161 A1 2/2014 Cully et al.
2014/0074144 A1 3/2014 Shrivastava et al.
2014/0155908 A1 6/2014 Rosenbluth et al.
2014/0243885 A1 8/2014 Eckhouse et al.
2014/0277015 A1 9/2014 Stinis
2014/0371779 A1 12/2014 Vale et al.
2015/0112376 A1 4/2015 Molaei et al.
2015/0157346 A1 6/2015 Ferrera et al.
2015/0164666 A1 6/2015 Johnson et al.
2015/0231360 A1 8/2015 Watanabe et al.
2015/0359547 A1 12/2015 Vale et al.
2016/0081704 A1 3/2016 Jeon et al.
2016/0256255 A9 9/2016 Ma
2017/0065299 A1 3/2017 Gillespie et al.
2017/0071614 A1 3/2017 Vale et al.
2017/0079767 A1 3/2017 Leon-Yip
2017/0105743 A1 4/2017 Vale et al.
2017/0119408 A1 5/2017 Ma
2017/0119409 A1 5/2017 Ma
2017/0215900 A1 8/2017 Lowinger et al.

(56) References Cited

U.S. PATENT DOCUMENTS

2017/0215902 A1 8/2017 Leynov et al.
2017/0239444 A1 8/2017 Parker
2017/0333060 A1 11/2017 Panian
2018/0028209 A1 2/2018 Sudin et al.
2018/0064454 A1 3/2018 Losordo et al.
2018/0116684 A1 5/2018 Garrison et al.
2018/0126132 A1 5/2018 Heilman et al.
2018/0132876 A1 5/2018 Zaidat
2018/0206862 A1 7/2018 Long
2018/0318062 A1 11/2018 Sudin et al.
2018/0353196 A1 12/2018 Epstein et al.
2018/0361114 A1 12/2018 Chou et al.
2019/0110805 A1 4/2019 Ulm, III
2019/0167284 A1 6/2019 Friedman et al.
2019/0167287 A1 6/2019 Vale et al.
2019/0216476 A1 7/2019 Barry et al.
2019/0239907 A1 8/2019 Brady et al.
2019/0269425 A1 9/2019 Sudin et al.
2019/0269491 A1 9/2019 Jalgaonkar et al.
2019/0274810 A1 9/2019 Phouasalit et al.
2019/0298396 A1 10/2019 Gamba et al.
2019/0307471 A1 10/2019 Friedman et al.
2019/0336727 A1 11/2019 Yang et al.
2020/0000613 A1 1/2020 Shrivastava et al.
2020/0008822 A1 1/2020 Eckhouse et al.
2020/0085444 A1 3/2020 Vale et al.
2020/0205838 A1 7/2020 Walzman
2020/0281612 A1 9/2020 Kelly et al.
2021/0000582 A1 1/2021 Chomas et al.
2021/0059695 A1 3/2021 Haran et al.
2021/0068852 A1 3/2021 Spence
2021/0077134 A1 3/2021 Vale et al.
2021/0177442 A1 6/2021 Girdhar et al.
2021/0236150 A1 8/2021 Arad Hadar
2021/0298775 A1 9/2021 Nguyen et al.
2021/0379350 A1 12/2021 Skillrud et al.
2021/0393279 A1 12/2021 O'Malley et al.
2021/0393280 A1* 12/2021 Cortiñas Villazón ........................ A61L 31/022
2022/0000500 A1 1/2022 Arad Hadar et al.
2022/0211400 A1 7/2022 Cox et al.
2022/0265962 A1 8/2022 Rios Garriga et al.
2022/0287765 A1 9/2022 Nageswaran et al.
2022/0354517 A1 11/2022 Behan
2022/0387051 A1 12/2022 Girdhar et al.
2022/0387098 A1 12/2022 Girdhar et al.
2023/0014731 A1 1/2023 Casey et al.
2023/0064470 A1 3/2023 Girdhar et al.
2023/0127145 A1 4/2023 Arad Hadar et al.
2023/0149021 A1 5/2023 Wainwright
2023/0210544 A1 7/2023 Gamba et al.
2023/0270461 A1 8/2023 Garcia Sabido et al.
2023/0301807 A1 9/2023 Garcia Sabido et al.
2024/0115280 A1 4/2024 Garcia Sabido et al.
2024/0115281 A1 4/2024 Garcia Sabido et al.
2024/0148395 A1 5/2024 Salmon et al.
2025/0032134 A1 1/2025 Salmon et al.
2025/0160865 A1 5/2025 Arad Hadar
2026/0007420 A1 1/2026 Salmon et al.

FOREIGN PATENT DOCUMENTS

CN 104159525 A 11/2014
CN 107198554 B 2/2020
EP 1427087 A1 6/2004
EP 2662109 A1 11/2013
EP 3266391 A1 1/2018
ES 2341978 T3 6/2010
ES 2381099 T3 5/2012
GB 2498349 A 7/2013
JP 2005500138 A 1/2005
WO WO99/45835 A2 9/1999
WO WO02/087677 A2 11/2002
WO WO03/075793 A1 9/2003
WO WO2004/002564 A1 1/2004
WO WO2005/027751 A1 3/2005
WO WO2008/124567 A1 10/2008
WO WO2008/157202 A1 12/2008
WO WO2009/014723 A1 1/2009
WO WO2009/105710 A1 8/2009
WO WO2011/068924 A1 6/2011
WO WO2011/082319 A1 7/2011
WO WO2012/106657 A2 8/2012
WO WO2012/156924 A1 11/2012
WO WO2012/158269 A1 11/2012
WO WO2013/008233 A1 1/2013
WO WO2013/152327 A1 10/2013
WO WO2014/008460 A2 1/2014
WO WO2014/127389 A2 8/2014
WO WO2014/204860 A1 12/2014
WO WO2015/006782 A1 1/2015
WO WO2015/189354 A1 12/2015
WO WO2016/113047 A1 7/2016
WO WO2017/072663 A1 5/2017
WO WO2017/074290 A1 5/2017
WO WO2017/075544 A1 5/2017
WO WO2018/080590 A1 5/2018
WO WO2018/160966 A1 9/2018
WO WO2019/055311 A1 3/2019
WO WO2019/064306 A1 4/2019
WO WO2019/178131 A1 9/2019
WO WO2020/021333 A2 1/2020
WO WO2020/079082 A1 4/2020
WO WO2020/099386 A1 5/2020
WO WO2021/016213 A1 1/2021
WO WO2023/117919 A1 6/2023

OTHER PUBLICATIONS

Arad et al.; U.S. Appl. No. 62/760,786 entitled "Thrombectomy system comprising an expandable tip aspiration catheter and clot-capture element," filed Nov. 13, 2018.

Berkhemer et al.; A randomized trial of intraarterial treatment for acute ischemic stroke; New England Journal of Medicine; 372; pp. 11-20; Jan. 1, 2015.

Bouthillier et al.; Segments of the internal carotid artery: a new classification; Neurosurgery; 38(3); pp. 425-433; Mar. 1, 1996.

Castano et al.; Unwanted detachment of the Solitaire device during mechanical thrombectomy in acute ischemic stroke; Journal of neurointerventional surgery; 8(12); pp. 1226-1230; Dec. 1, 2016.

Ceretrieve; 3 pages; retrieved from the internet (http://trendlines.com/portfolio/ceretrieve/) on Sep. 13, 2018.

Duffy et al.; Novel methodology to replicate clot analogs with diverse composition in acute ischemic stroke; Journal of neurointerventional surgery; 9(5); pp. 486-491; May 1, 2017.

Fennell et al.; What to do about fibrin rich "tough clots"? Comparing the Solitaire stent retriever with a novel geometric clot extractor in an in vitro stroke model; Journal of neurointerventional surgery; 10(9); pp. 907-910; Sep. 1, 2018.

Medtronic; Medtronic.com; The Solitaire Platinum Revascularization Device; Model Specifications; DC00079632 Rev A ; 1 page; retrived from the internet (https//www.medtronic.com) on Mar. 2018.

Mokin et al.; Stent retriever thrombectomy with the Cover accessory device versus proximal protection with a balloon guide catheter: in vitro stroke model comparison; Journal of neurointerventional surgery; 8(4); pp. 413-417; Apr. 1, 2016.

Penumbra Inc.; Recalls 3D revascularization device due to wire material that may break or separate during use; FDA Recall; retrieved from the internet (http:/web.archive.org/web/20200813123505/https:/www.fda.gov/medical-devices/medical-device-recalls/penumbra-ino-recalls-3d-revascularization-device-due-wire-material-may-break-of-separate-during-use).

Villazón et al., U.S. Appl. No. 18/641,098 entitled "Device and a thrombectomy apparatus for extraction of thrombus from a blood vessel", filed Apr. 19, 2024.

(56) References Cited

OTHER PUBLICATIONS

Garcia Sabido et al.; U.S. Appl. No. 18/722,456 entitled "An intravascular device with an improved attachment of its elements and a method of manufacturing thereof," filed Jun. 20, 2024.

* cited by examiner

INTRAVASCULAR DEVICE WITH AN IMPROVED ATTACHMENT OF ITS ELEMENTS AND A METHOD OF MANUFACTURING THEREOF

TECHNICAL FIELD

The present invention is directed, in general, to the field of medical devices to restore blood flow or remove thrombus. In particular, the invention relates to an intravascular catheter device with an improved attachment of its elements, such that the intravascular device is adapted to be safely maneuvered/manipulated during a medical intervention. The invention also relates to a method for connecting a tool to a vascular catheter to enable the vascular catheter to maneuver the tool.

BACKGROUND OF THE INVENTION

Intravascular catheters to restore blood flow or remove thrombus from a blood vessel during a thrombectomy intervention have to be advanced, pulled and kept intact within the blood vessel during the intervention. Control and advancement of such devices is challenging as they must undergo push, pull and torque moves. Because of the length of these catheter devices and the movements and forces that the user must apply to them during the thrombectomy intervention, it is often difficult to maintain a strong attachment/connection of the elements that are part of the catheter.

WO2019168737 discloses example catheters including an elongated body comprising an inner liner, an outer jacket, a structural support member positioned between at least a portion of the inner liner and at least a portion of the outer jacket, and an expandable member distal to the structural support member at a distal portion of the elongated body. The expandable member is configured to expand radially outward within a vessel of a patient, e.g., to engage a clot. In some embodiments, the outer jacket may be heat shrunk around the structural support member and a proximal portion of the expandable member. In none of the embodiments does the inner liner extend beyond the outer jacket to form a distal connection portion to be secured to the expandable member by an attachment.

US2021000582 discloses a deployable apparatus that is useful in an embolization procedure, and which enables substantially unrestricted forward flow of blood in a vessel and reduces or stops reflux (regurgitation or backward flow) of embolization agents which are introduced into the blood. In some embodiments, the deployable apparatus includes a delivery catheter having a valve fixedly coupled to its distal end. An outer catheter is provided which extends over the valve during introduction to maintain the valve in a collapsed cylindrical configuration until the valve is advanced through the patient to the desired vascular destination. Once at the destination, the outer catheter is retracted from over the valve to permit expansion of the valve into an open state, as discussed above. The valve can be attached to the distal end of the catheter by a sleeve that is bonded or mechanically held by a heat shrink process or other mechanical process to the catheter. In another embodiment, the valve is fused into the catheter by a chemical process or by thermally melting the valve, the catheter or both. The catheter lacks an inner catheter element extending beyond an outer jacket and serving as a distal connection portion to be secured to the expandable valve by an attachment.

However, current catheter devices for blood flow restoration or thrombus removal often break or separate during use, which may cause serious health consequences to the patients.

Besides the above, nowadays, braid meshes are cut with mechanical cut techniques, such as shears like scissors or snips. These mechanical cuts usually generate tensional stress, compressional stress and shear stress to the object (e.g., the wire ends). Moreover, those techniques can generate traumatic ends (e.g., wire ends) due to stress results. For example, mechanical cut techniques can generate flaring on the wire ends, i.e., the wire ends are not cut in the same cross-sectional axis and the wire ends can be outwardly or inwardly disposed.

New intravascular devices with improved navigability and attachment of the elements/components thereof are therefore needed.

DESCRIPTION OF THE INVENTION

Intravascular devices have to be advanced, pulled and kept intact within blood vessels during interventions, despite the moves that the devices must undergo (e.g., push, pull and torque moves). Such devices must be suitable for navigating through the vasculature without breaking and separating during use and cannot comprise traumatic elements, to avoid health consequences and to provide a proper safety configuration. For all these reasons, it is often difficult to connect/attach the elements of the device while preserving all those conditions.

Thus, an object of the present invention is to provide an intravascular device with an improved attachment of its elements. Similarly, an object of the present invention is to also provide a method for connecting a tool to a vascular pusher to enable the vascular pusher to maneuver the tool.

The invention is defined by the attached independent claims. Embodiments are described in the dependent claims.

According to one aspect, the present invention provides an intravascular device, particularly, to be advanced through neurovasculature, with an improved attachment of its elements. The intravascular device includes a vascular pusher comprising a distal connection portion; a tool (e.g. a funnel, an expandable capture element, or other medical device) attached to, and extending from, the distal connection portion of the vascular pusher, the tool being formed by a mesh of at least two sets of filaments and comprising a proximal connection portion that includes laser-cut proximal ends of the at least two sets of filaments; and an attachment between the tool proximal connection portion and the vascular pusher distal connection portion adapted to keep the tool connected to the vascular pusher, the attachment having an outer diameter substantially equal to an outer diameter of the vascular pusher.

Therefore, the proposed intravascular medical device for restoring blood flow or remove thrombus has an improved attachment between its elements enhancing navigability through the vessels, avoiding damaging the vessels, and enabling movement of concentric internal medical devices such as microcatheters within the intravascular device. This is achieved by the cited attachment having an outer diameter substantially the same as, or less than, the vascular pusher outer diameter.

Furthermore, the proposed intravascular device, an in particular the proximal connection portion, is atraumatic and avoids flaring on the filament (or wire) ends. Moreover, the intravascular device maintains flexibility in a distal end of the tool and avoids elongation and detachment.

Indeed, due to the atraumatic ends, the connection between the tool and the vascular pusher provides an attachment with safer and better mechanical connection, avoiding separation, elongation, and traumatic elements.

For purposes of the disclosure, "substantially" means that the diameter of the attachment, over the proximal connection portion of the tool and the distal connection portion of the vascular pusher, has to be similar to the diameter of the vascular pusher to accomplish with the requirements for a desired navigation through the blood vessel. Safety of the pusher is also improved; hence avoiding vessel wall damage and being suitable to navigate through the tortuosity of the paths. A substantially different diameter could generate irregularities in the navigability of the pusher through the blood vessel and could induce vessel damage.

For reasons of the disclosure of the present invention, "between" means the relation between elements/objects, not directly/necessarily the disposition thereof.

According to the present invention, the vascular pusher can comprise any of a hypotube, a vascular catheter or a tubular element.

In an embodiment, the laser-cut proximal ends don't extend outwardly or inwardly but they are disposed within or in a same cylindrical boundary (i.e., an imaginary cylinder that is concentric to an axial axis of the tool and that contains the tool proximal connection portion).

In some embodiments, the laser-cut proximal ends are disposed in the same cross-sectional (or radial) plane.

In some embodiments, the laser-cut proximal ends comprise perpendicular cross-sections with regard to the axial axis of the tool, i.e., the laser-cut proximal ends terminate in the same cross-sectional plane.

In an embodiment, the attachment comprises a thermoplastic material extending between the proximal connection portion of the tool and the distal connection portion of the vascular pusher.

In another embodiment, the attachment comprises a thermoplastic material extending over the proximal connection portion of the tool and over the distal connection portion of the vascular pusher.

The thermoplastic material can extend (when flowing) between and/or over the proximal connection portion and the distal connection portion.

In an embodiment, the inner catheter element (e.g., inner liner and/or braided layer) comprises openings (or cells) and the thermoplastic material of the attachment extends through the openings.

In an embodiment, the attachment comprises glue (or any other suitable adhesive material) extending between the proximal connection portion of the tool and the distal connection portion of the vascular pusher.

In another embodiment, the attachment comprises glue (or any other suitable adhesive material) extending over the proximal connection portion of the tool and the distal connection portion of the vascular pusher.

In an embodiment the mesh comprises two distinct tubular sections, a first tubular section (neck) of uniform diameter and a second tubular section (conical) comprising a shape with a progressive reduction of diameter to open and create a space for a thrombus, the first tubular section including the proximal connection portion of the tool.

In an embodiment, the mesh further comprises a third tubular section (tubular) of uniform diameter. The third tubular section is disposed in a distal end of the second tubular section, the distal end of the second tubular section having a diameter equal to a proximal end of the third tubular section; and a proximal end of the second tubular section having a diameter equal to a distal end of the first tubular section.

In an embodiment, the tool comprises three sections (neck-proximal-, conical and tubular-distal-) with a mesh/braid of at least two sets, equals or different, of filaments.

The filaments can be made of a shape memory material.

More particularly, the filaments can be made of a metal, a metal alloy or a composite including, among others, nitinol or nitinol/platinum, or also Niti #1-DFT® (Drawn Filled Tube), with a percentage of platinum from 10% to 40%; in particular with 20% platinum (Niti #1-DFT®-20% Pt) or 40% platinum (Niti #1-DFT®-40% Pt).

In some embodiments the tool is an expandable funnel. More in particular, a self-expandable funnel.

In an embodiment, the laser-cut proximal ends are cut by means of a laser beam. Mechanical cutting produces intricate shape cuts while laser cutting enables producing an accurate cut of the tool proximal end, affecting only a small area, which results in cleaner edges and in a minimization of the warping and distortion of the filaments. Some other advantages achieved by laser cutting are higher flexibility and precision, repeatability, speed, cost-effectiveness, better quality, contactless cutting, versatility and automation.

In some embodiments, the tool can also comprise a coating. In some embodiments, the coating can extend over at least part of the proximal connection portion, not extend over the proximal connection portion at all, or extend over at least a part of the attachment. In a particular embodiment, the coating extends over at least part of the proximal connection portion. In another particular embodiment, the coating extends over at least a part of the attachment. In some embodiments the coating can be non-permeable, thus enabling partially or totally stopping blood flow. In an embodiment, the coating can comprise an elastomeric or thermoplastic elastomer material such as polyurethane or silicone, among others.

According to another aspect, the present invention also provides a method of manufacturing an intravascular device, in particular, a method for attaching a tool formed by a mesh of at least two sets of filaments and comprising a proximal connection portion including laser-cut proximal ends of the at least two sets of filaments to a distal connection portion of a vascular pusher (e.g., a hypotube, a vascular catheter or a tubular element, among others). Particularly, the method comprises attaching the tool to the vascular pusher, extending from the distal connection portion of the vascular pusher, and creating/providing an attachment between (i.e., relation between elements/objects) the proximal connection portion and the distal connection portion to keep the tool connected to the vascular pusher, the attachment having an outer diameter substantially equal to an outer diameter of the vascular pusher.

In an embodiment, the laser-cut proximal ends are cut by means of a laser-cut technique. In an embodiment, the laser-cut proximal ends are cut by means of a laser device.

The laser device can be a fiber laser, a $CO_2$ laser, or an Nd or Nd-YAG laser, among others. In some embodiments, the laser device can operate at a wavelength near 1 micron, at a frequency near 100 KHz, and at a speed near 100 mm/second.

In some embodiments, the cutting time/duration of the proximal ends is between 1 and 5 seconds.

In an embodiment, the wavelength of the laser device is 1064 nm, that is, the laser device emits in the infrared.

In an embodiment, the laser-cut proximal ends of the filaments are disposed within or in a same cylindrical (or radial) boundary, without extending outwardly or inwardly.

In an embodiment, the laser-cut proximal ends terminate in the same cross-sectional (or radial) plane.

In an embodiment, the laser-cut proximal ends comprise perpendicular cross-sections with regard to an axial axis of the tool.

In an embodiment, the step of creating/providing an attachment comprises applying energy to cause a thermoplastic material to flow between the proximal connection portion and the distal connection portion. Particularly, heat shrinking is applied, for instance using a heat shrinking tube (HST), which is disposed concentrically over the vascular catheter and applies pressure to adjust the diameter and then heat is applied to melt the shrinking material and fuse it to other materials (e.g., inner liner or braided layer).

In some embodiments, the step of creating an attachment can include applying glue to the proximal connection portion and the distal connection portion.

In some embodiments, the step of applying glue can include applying glue over the proximal connection portion and permitting the glue to flow through openings in the proximal connection portion to the distal connection portion.

In some embodiments, the step of applying glue comprises applying glue between the proximal connection portion and the distal connection portion.

In some embodiments the glue is cured. This can be done by means of applying energy, for instance, but not limited to, by applying light such as UV light. Alternatively, or complementary, curation of the glue can be done via other means, for example by humidity, waiting some time.

In some embodiments, the method further comprises applying a coating to at least part of the tool. In other embodiments, the coating can be applied to the proximal connection portion of the tool, to at least part of the proximal connection portion, or to at least a part of the attachment.

In other embodiments, the intravascular device comprises the vascular pusher (particularly, a vascular catheter) and the tool (e.g., a funnel, an expandable capture element, or other medical device) of the previous embodiments. The vascular catheter comprises a catheter jacket and an inner catheter element surrounded by the catheter jacket, and the distal connection portion of the vascular catheter comprises an extended portion of the inner catheter element extending distally beyond a distal end of the catheter jacket. The tool is attached to, and extends from, the distal connection portion of the vascular catheter, and is formed by a mesh of at least two sets of filaments and comprises a proximal connection portion that includes laser-cut proximal ends of the at least two sets of filaments, the laser-cut proximal ends abutting the inner catheter element. The intravascular device also comprises the attachment between the tool proximal connection portion and the vascular catheter distal connection portion to keep the tool connected to the vascular catheter, the attachment having an outer diameter substantially equal to an outer diameter of the vascular catheter.

In an embodiment, the attachment extending over the extended portion of the inner catheter element and over the laser-cut proximal ends of the proximal connection portion of the tool.

In an embodiment, the inner catheter element comprises a first element (e.g., an inner liner) and a second element, the laser-cut proximal ends of the proximal connection portion of the tool abutting a distal end of the second element.

In an embodiment, the first element comprises a polymer material, such as polytetrafluoroethylene (PTFE), among others.

More particularly, the inner liner is disposed within the catheter jacket.

The catheter jacket can be made of any suitable thermoplastic material or elastomeric/elastomer material, e.g., polyether block amide (PEBAX®) with shore 25, 35, 40, 55, 63 or 72D. In a particular embodiment, the catheter jacket is made of a thermoplastic material, more particularly of PEBAX® 40D.

In some embodiments, the second element of the inner catheter element can comprise a braided layer.

In an embodiment, the inner catheter element further comprises a braided layer disposed within the catheter jacket (i.e., the inner liner is surrounded by the braided layer).

Particularly, the braided layer is concentrically disposed within the catheter jacket. The braided layer can be made of e.g., stainless steel, nitinol, liquid crystal polymer (LCP), etc. Particularly, it is made of nitinol.

In an embodiment, the distal connection portion of the vascular catheter comprises a distal portion of the inner liner extending distally beyond the distal end of the catheter jacket. In some embodiments, the distal portion of the inner liner extends distally beyond the distal end of the braided layer.

In an embodiment, the distal connection portion of the vascular catheter comprises a portion of the braided layer extending distally beyond the distal end of the catheter jacket.

In an embodiment, the laser-cut proximal ends of the proximal connection portion of the tool abut (i.e., without a substantial gap and without overlapping) a distal end of the braided layer. Therefore, kinking of the intravascular device is avoided.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF THE INVENTION AND OF PARTICULAR EMBODIMENTS

This disclosure describes an intravascular device, configured to be advanced through neurovasculature, with an improved attachment between its elements and a corresponding method for manufacturing such intravascular device. It should be noted that even though in some of the attached figures the elements/layers are shown with gaps therebetween, in the final assembly of the intravascular device those gaps are not present as the different materials of the elements/layers flow and fuse between them. Therefore, the figures illustrate the disposition/relation between elements, objects and layers of the present invention.

Figure 1A:
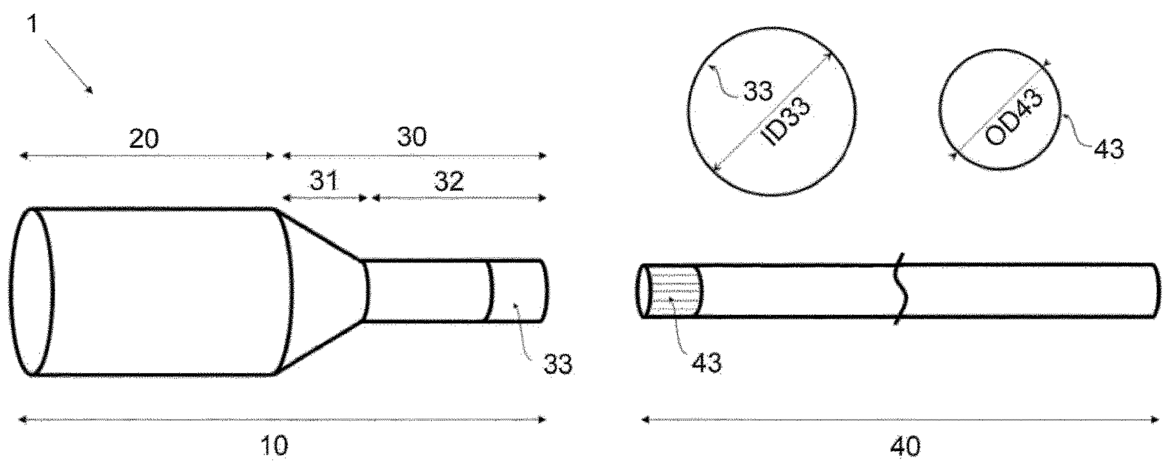
FIGS. 1A-B schematically illustrate an intravascular device and the relation of cross-sections between the vascular catheter and the tool included in the proposed intravascular device, according to an embodiment of the present invention.
Figure 1B:
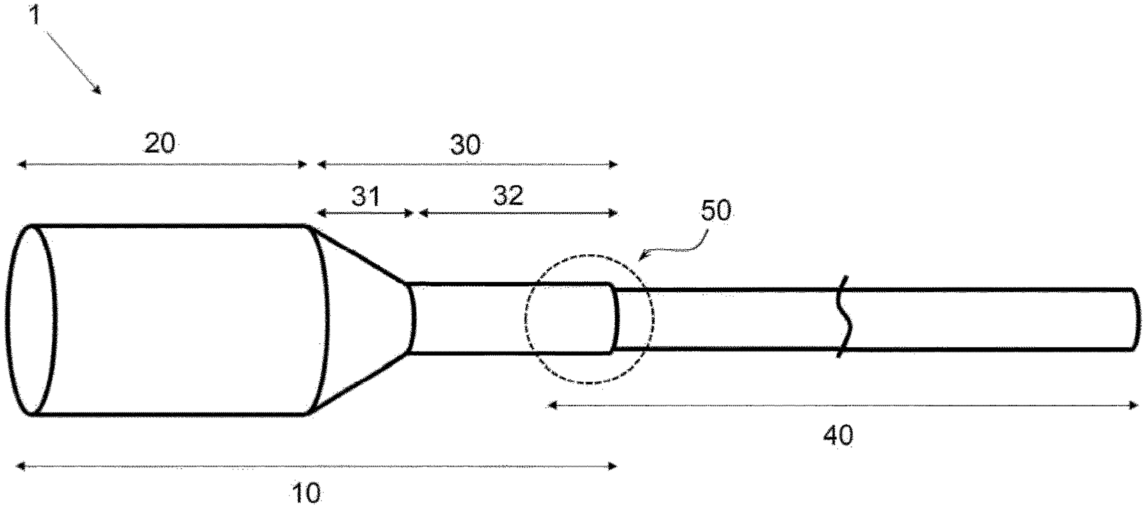

With reference to FIGS. 1A and 1B, therein an embodiment of the proposed intravascular device 1 is shown. The intravascular device 1 comprises a vascular device 40 and a tool 10 comprising a proximal connection portion 33. As seen in FIG. 1B, the tool 10 is attached to, and extend from, a distal connection portion 43 of the vascular device 40 (in this particular case a vascular catheter) via an attachment 50, by means of the proximal connection portion 33 of the tool. The attachment 50 comprises an outer diameter substantially equal to an outer diameter of the vascular catheter 40. The relation of diameters of the proximal connection portion 33 and the distal connection portion 43 is schematically shown in FIG. 1A.

The tool 10 can comprise different medical devices, particularly an expandable funnel, and includes two tubular sections, a second tubular section 20 and a first tubular section 30 proximal to the second tubular section 20. Particularly, the first tubular section 30 comprises two sub sections, a first sub section 32 and a second sub section 31. In the embodiment of FIGS. 1A and 1B, the second subsection 31 is cone-shaped or funnel-shaped and the first sub section 32 comprises the proximal connection portion 33.

FIGS. 2A-2G schematically illustrate another embodiment of the intravascular device 1. FIGS. 3A-3G illustrate a cross-sectional view of the intravascular device of FIGS. 2A-2G, comprising a vascular catheter 40 and a tool 10. The vascular catheter 40 includes a catheter jacket 44, which is formed from a thermoplastic or elastomeric/elastomer material such as PEBAX® with shore 25, 35, 40, 55, 63 or 72D, and an inner catheter element surrounded by the catheter jacket 44. A distal connection portion 43 of the vascular catheter 40 comprises an extended portion of the inner catheter element extending distally beyond a distal end of the catheter jacket 44.

According to this embodiment, the inner catheter element comprises an inner liner 46 and a braided layer 45, both concentrically disposed within the catheter jacket 44.

According to the invention, the inner liner 46 is made of a polymer material. The inner liner 46 is surrounded by the braided layer 45, which is made of, but not limited to, a metal material or metal alloy such as stainless steel or nitinol.

In some embodiments, the braided layer 45 can extend distally beyond the distal end of the catheter jacket 44, and the inner liner 46 can extend distally beyond a distal end of the braided layer 45.

Figure 2A:
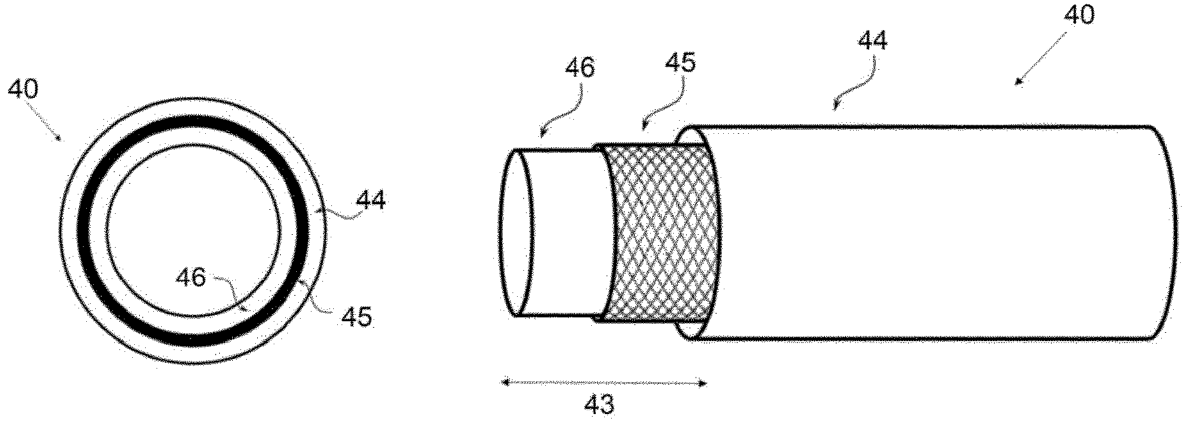
FIGS. 2A-2G schematically illustrate an intravascular device, according to an embodiment of the present invention.
Figures 2B, 2C, 2D:
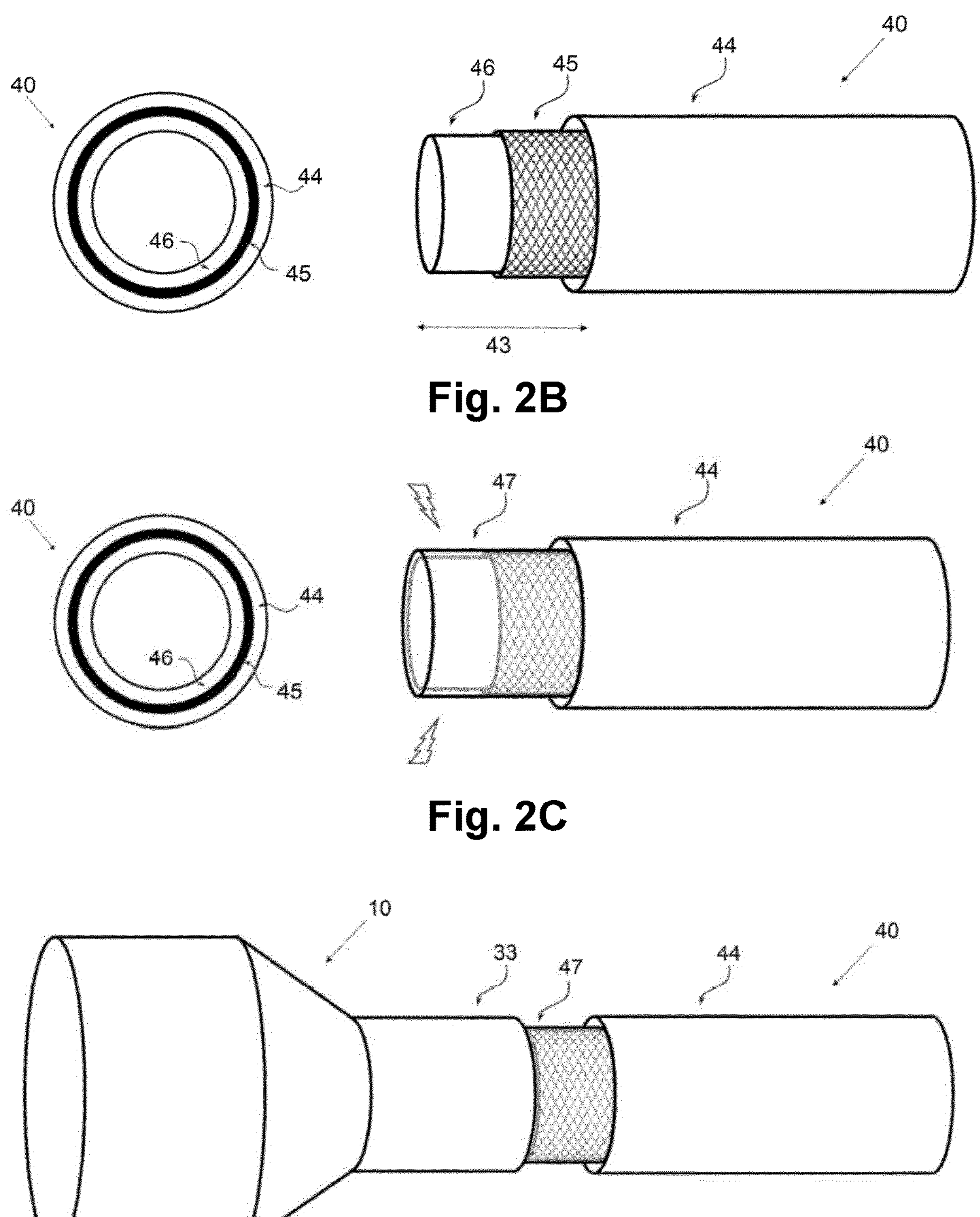
Figure 3A:
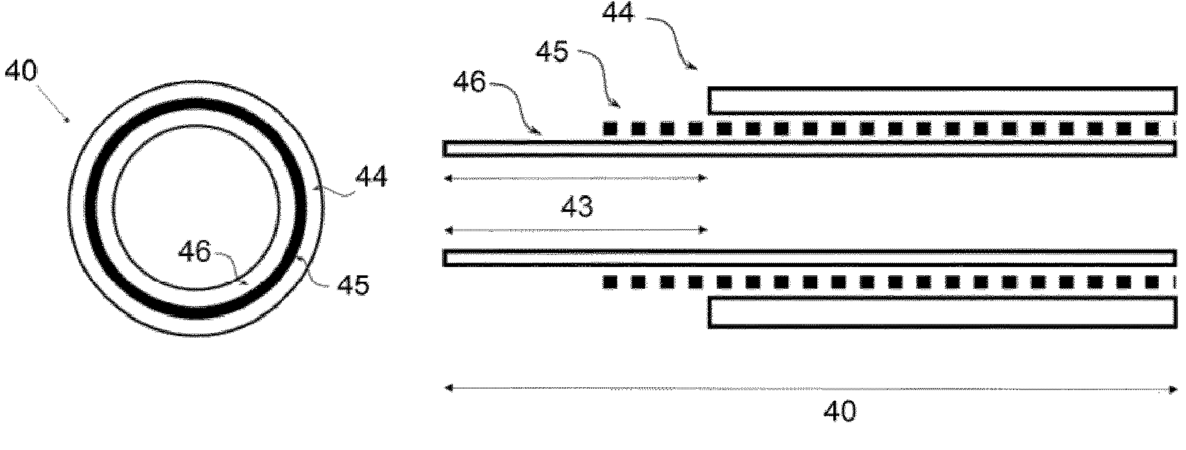
FIGS. 3A-3G schematically illustrate a longitudinal cross-sectional view of the vascular catheter shaft, the tool and the attachment included in the proposed intravascular device of FIGS. 2A-2G.
Figure 3B:
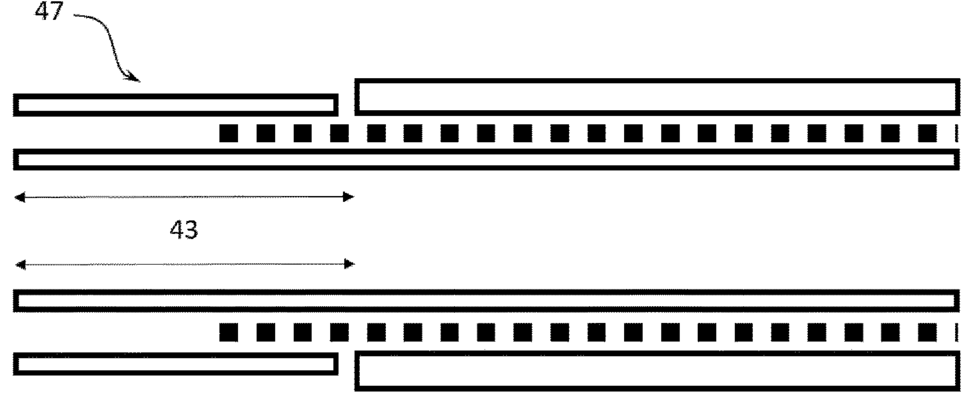
Figure 3C:
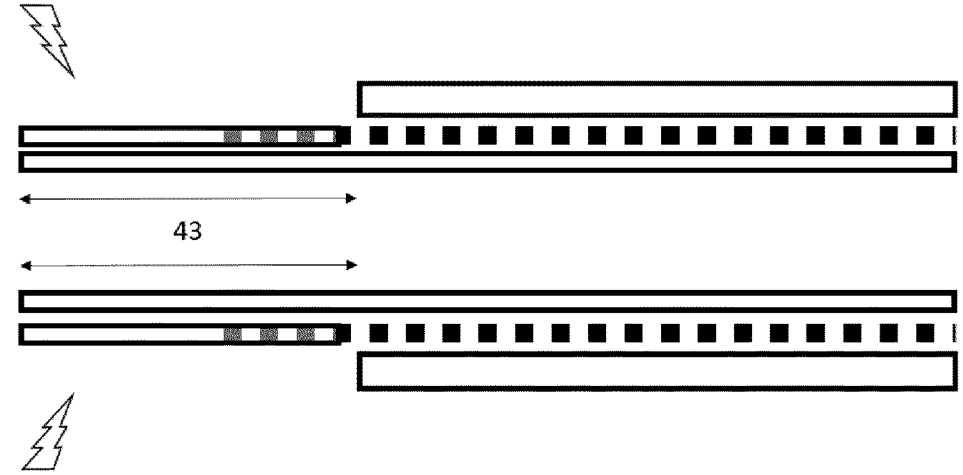
Figure 3D:
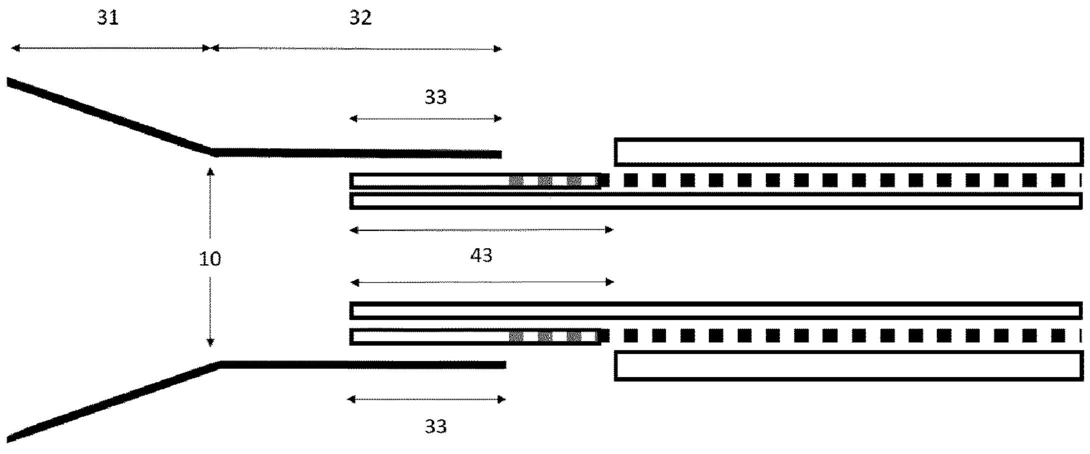

Besides the above-described elements, in an embodiment, an inner thermoplastic material or inner jacket 47 is placed around a portion of the inner catheter element (comprising the inner liner 46 and/or the braided layer 45) extending distally beyond the distal end of the vascular catheter 44 (see FIGS. 2B and 3B). The inner thermoplastic material or inner jacket 47 is made of, but not limited to, PEBAX® with shore 25, 35, 40, 55, 63 or 72D, particularly 55D. As seen in FIGS. 2C and 3C, heat is applied to allow the inner jacket 47 to flow into the braided layer 45 and onto the inner liner 46.

Figure 2E:
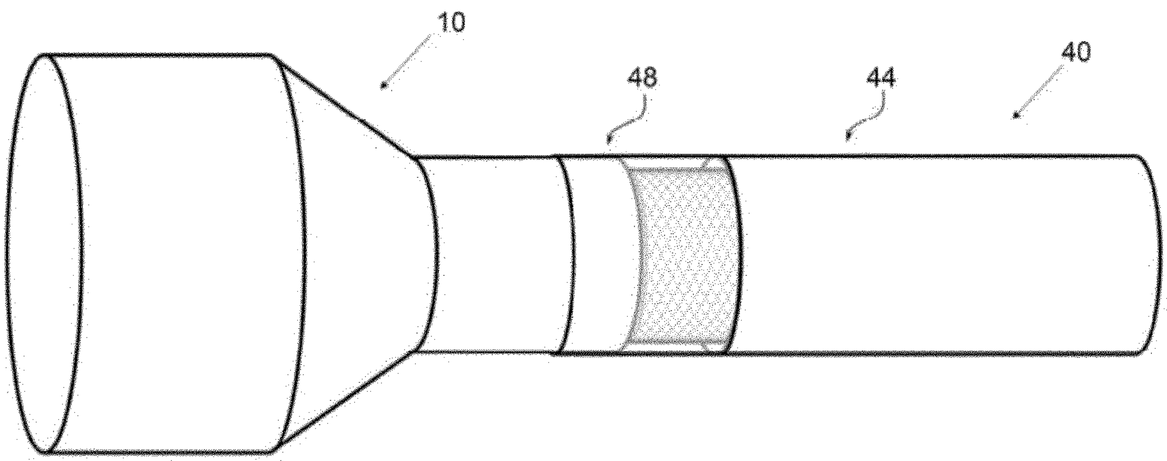
Figure 2F:
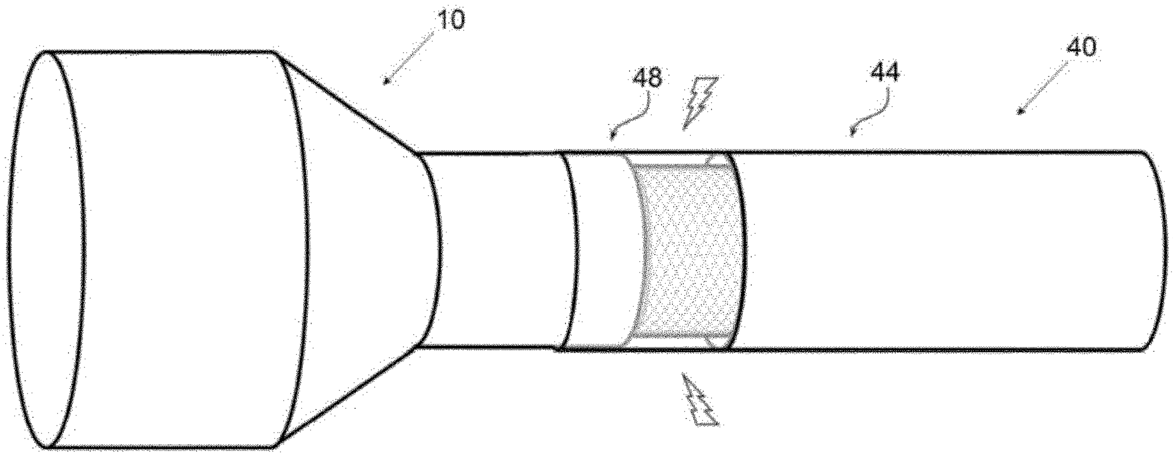
Figure 2G:
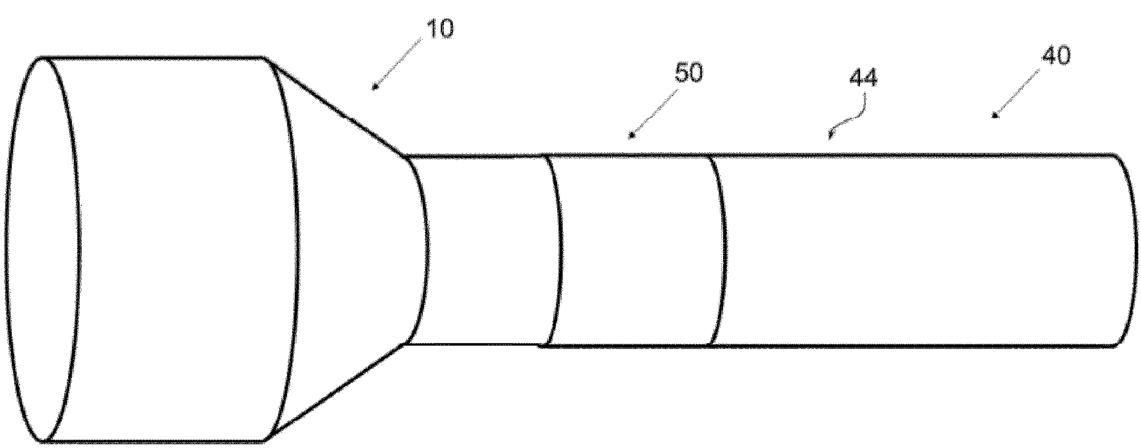
Figure 3E:
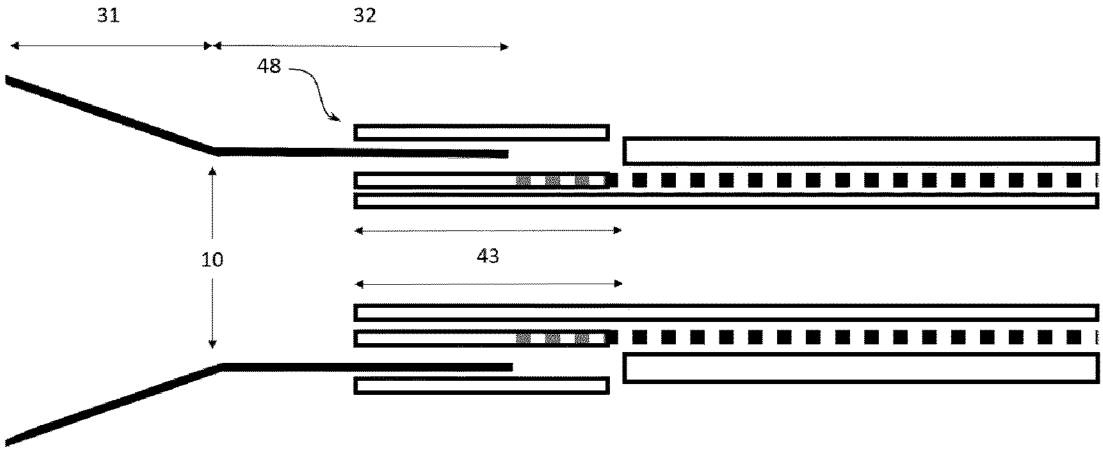
Figure 3F:
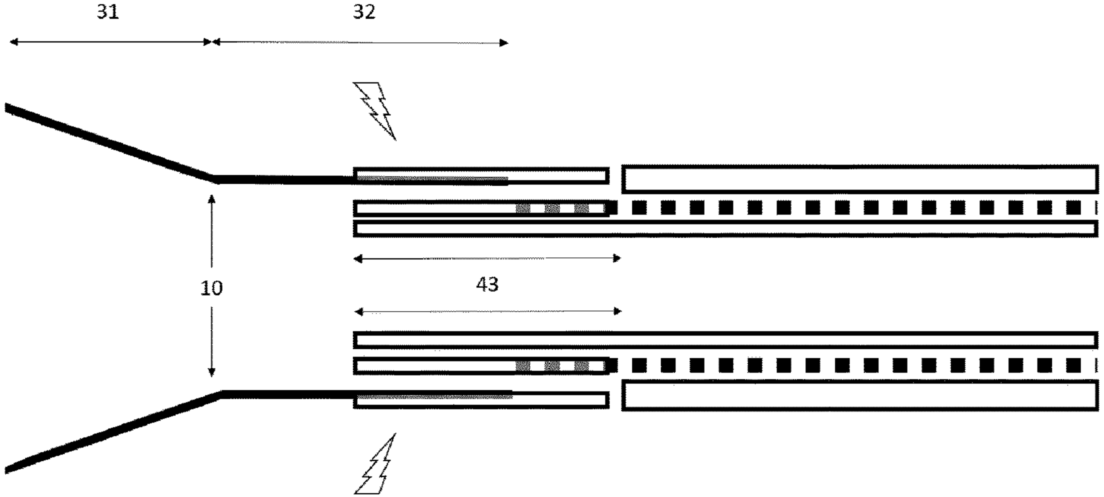
Figure 3G:
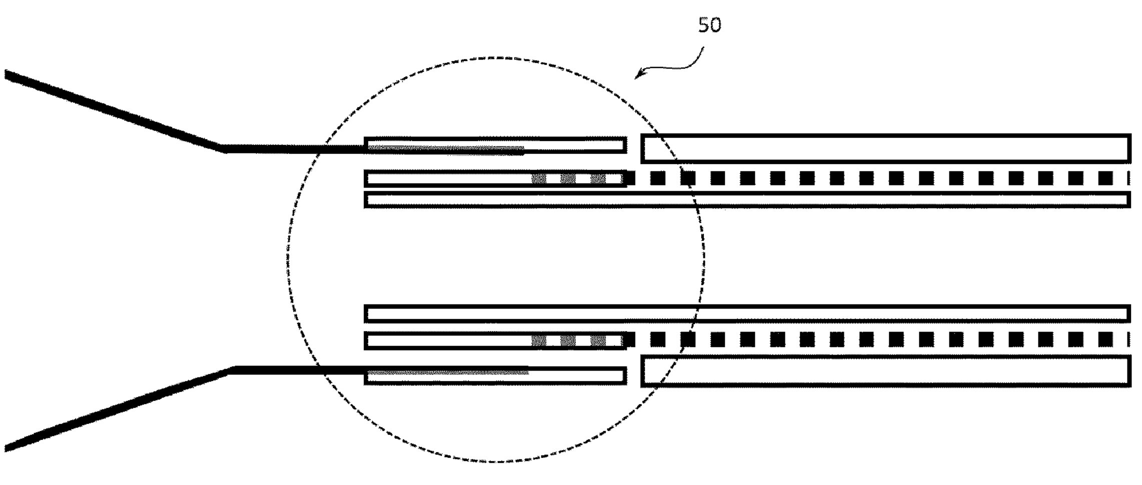
Figure 4A:
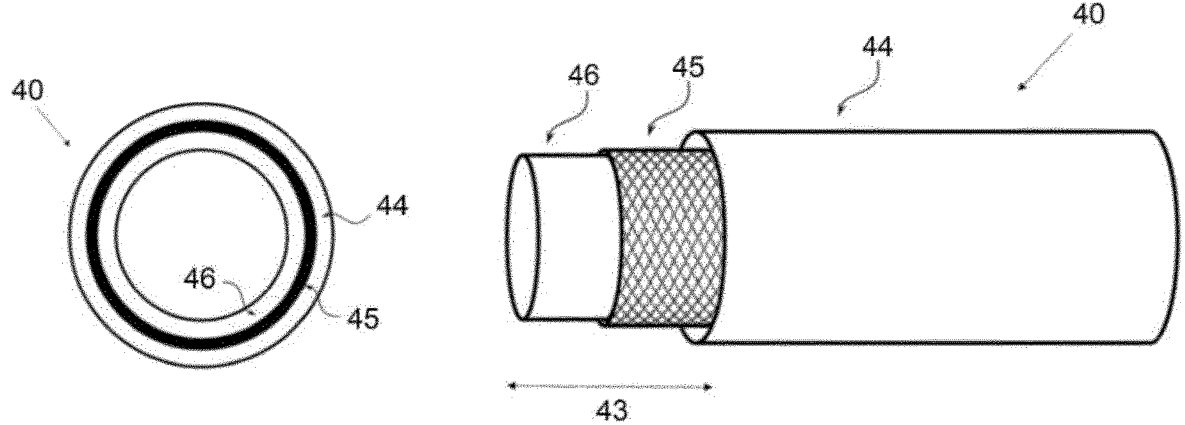
FIGS. 4A-4E schematically illustrate an intravascular device, according to an embodiment of the present invention.
Figure 4B:
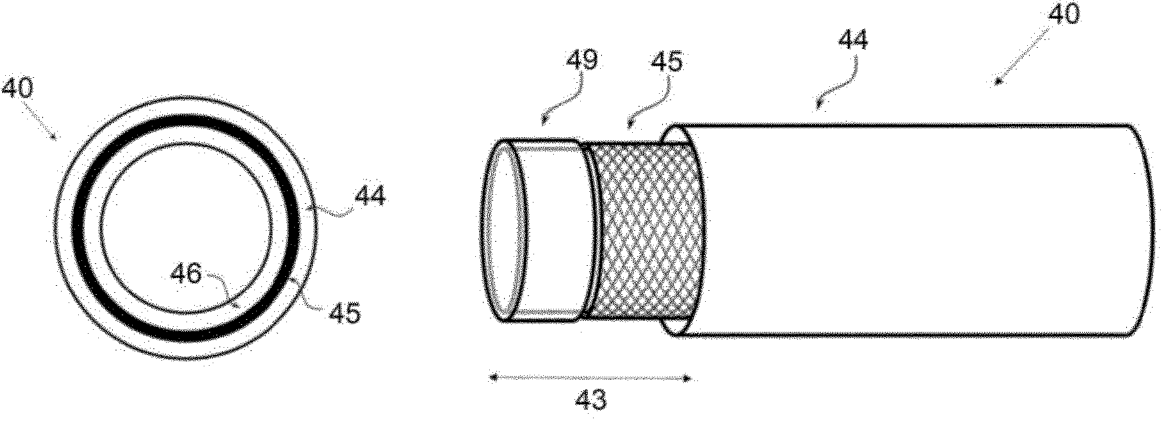
Figure 4C:
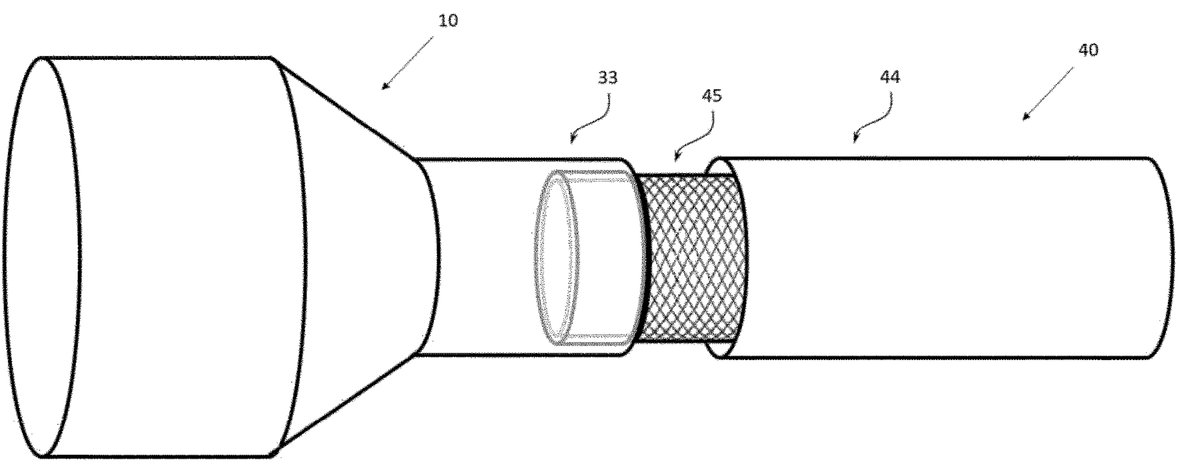
Figure 4D:
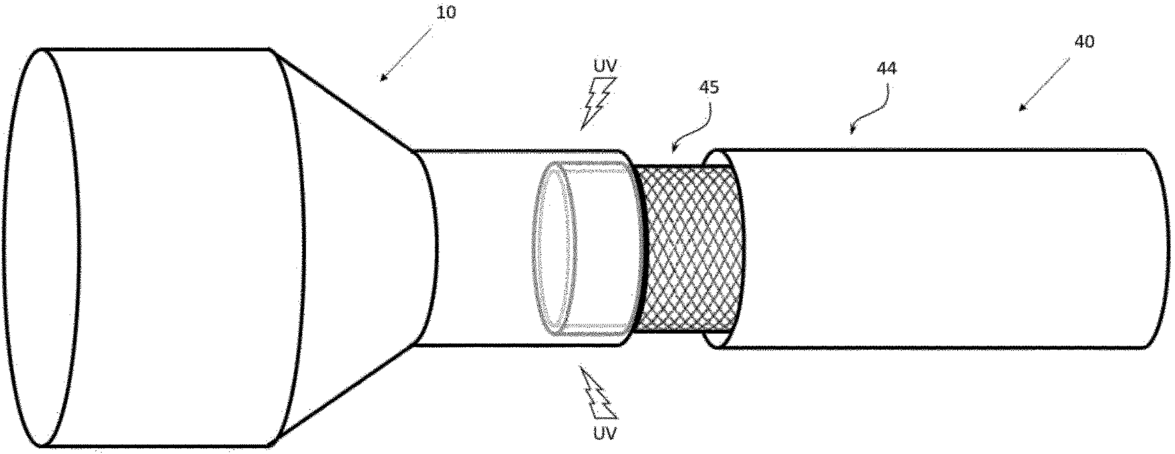
Figure 4E:
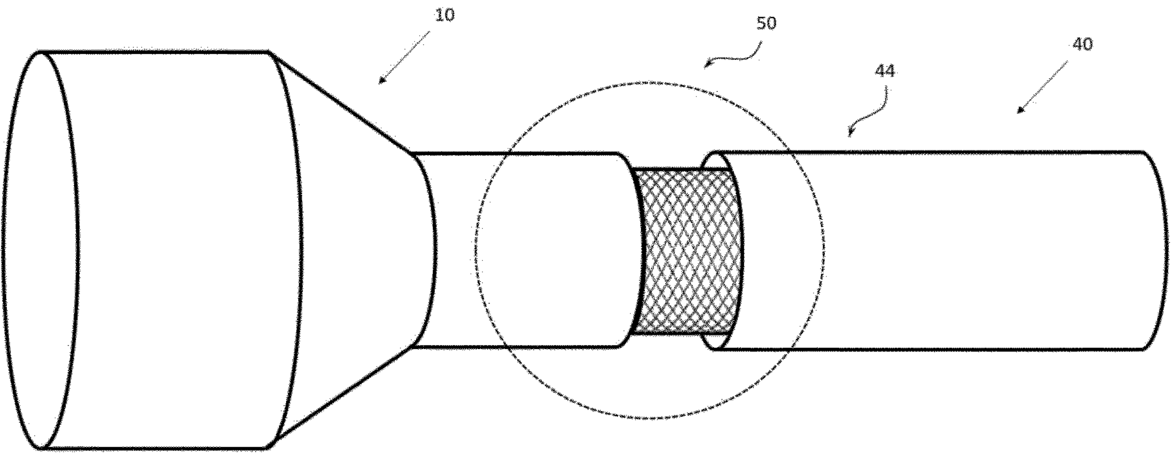
Figures 5A, 5B, 5C:
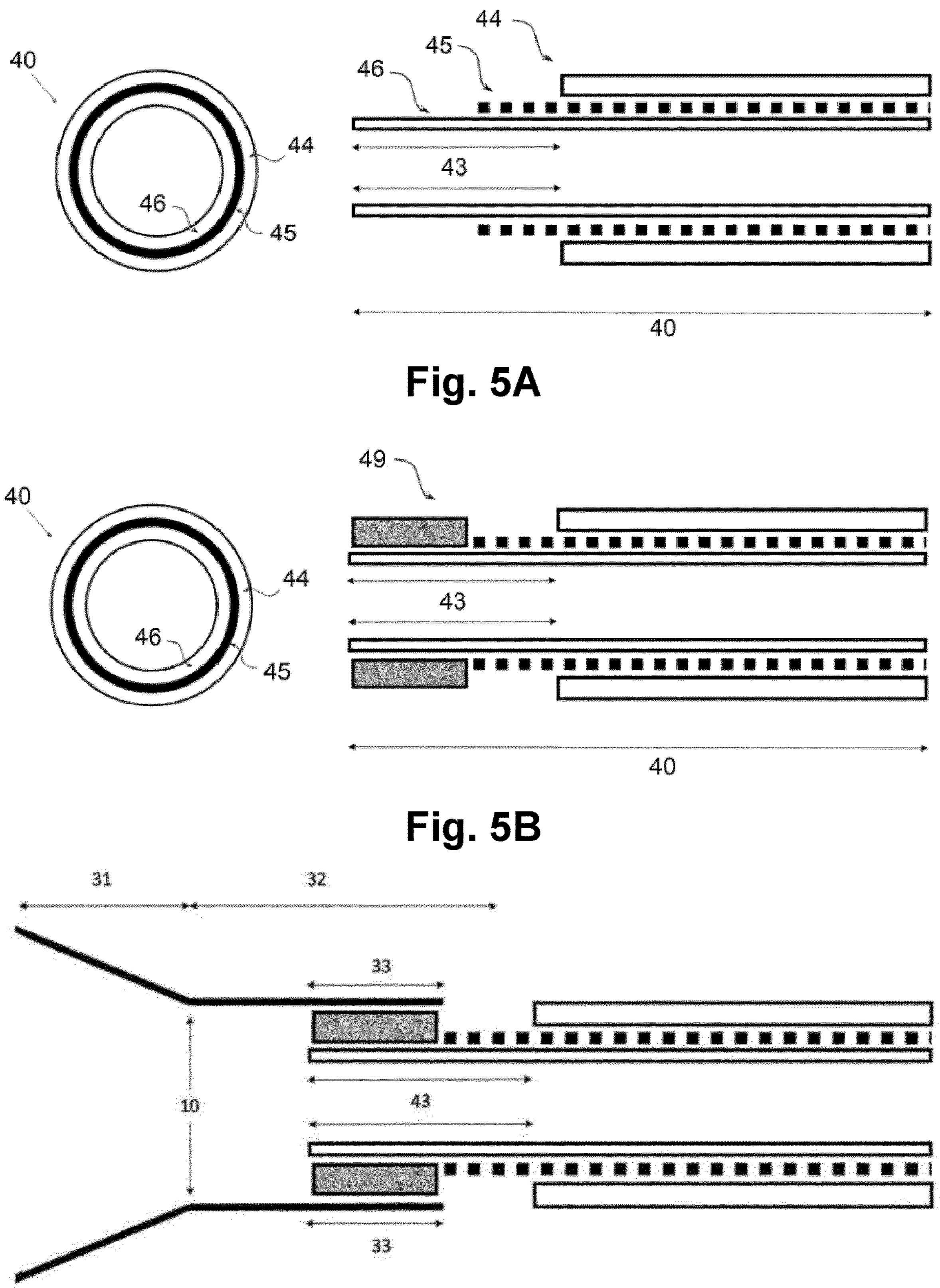
FIGS. 5A-5E schematically illustrate a longitudinal cross-sectional view of the vascular catheter shaft, the tool and the attachment included in the proposed intravascular device of FIGS. 4A-4E.
Figures 5D, 5E, 6A:
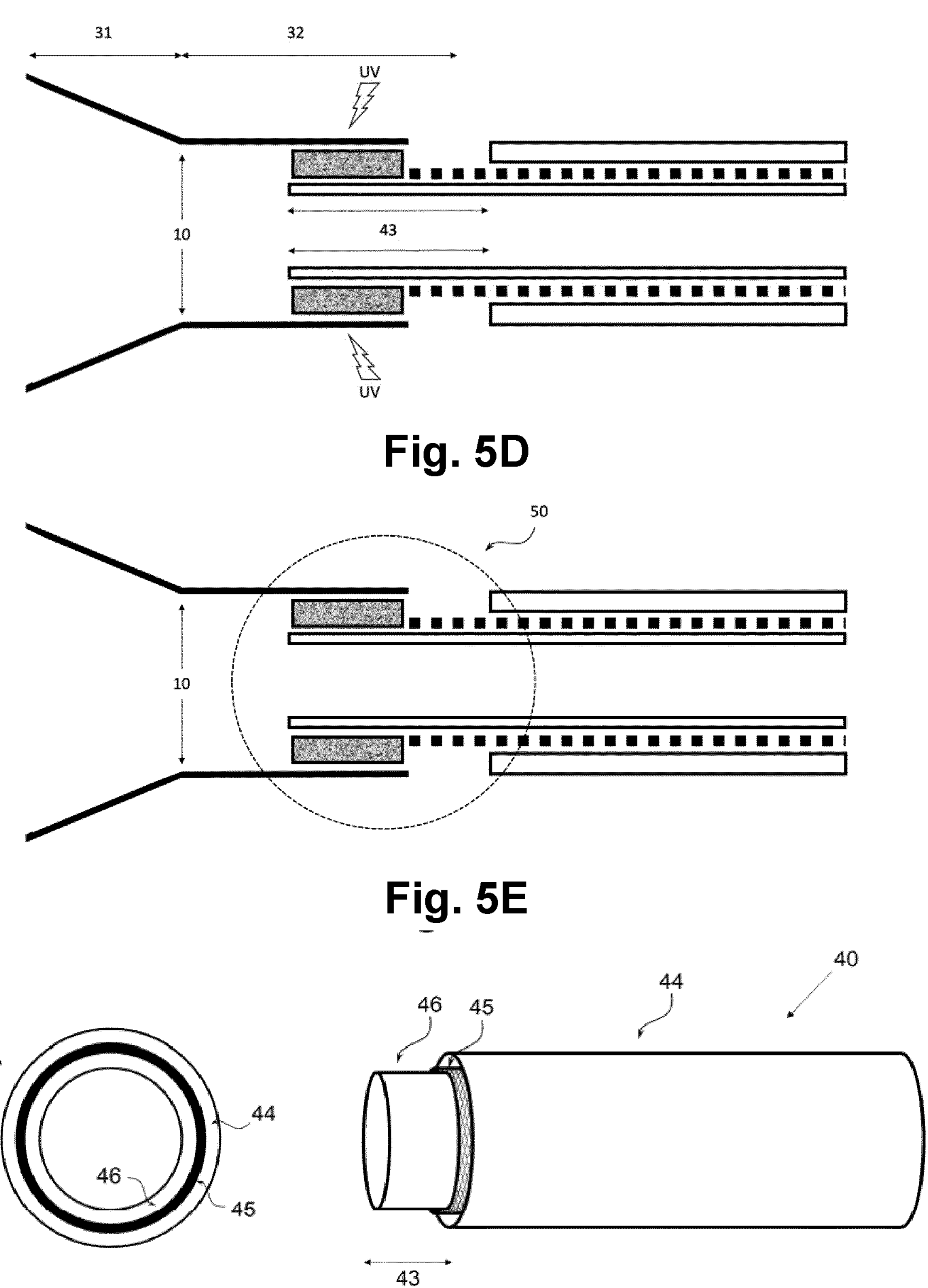
FIGS. 6A-6D schematically illustrate another intravascular device, according to an embodiment of the present invention.
Figures 6B, 6C, 6D:
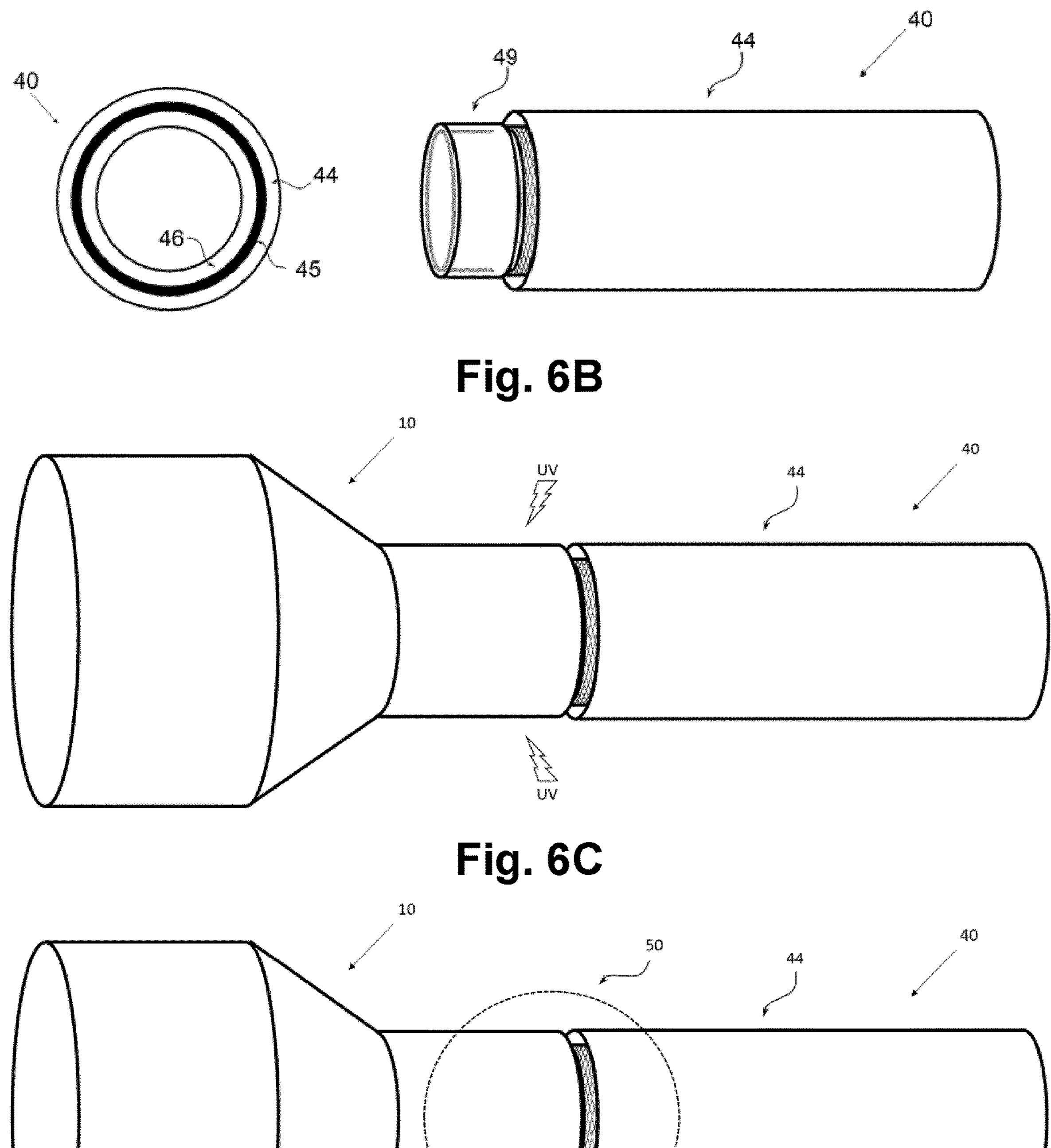
Figure 7A:
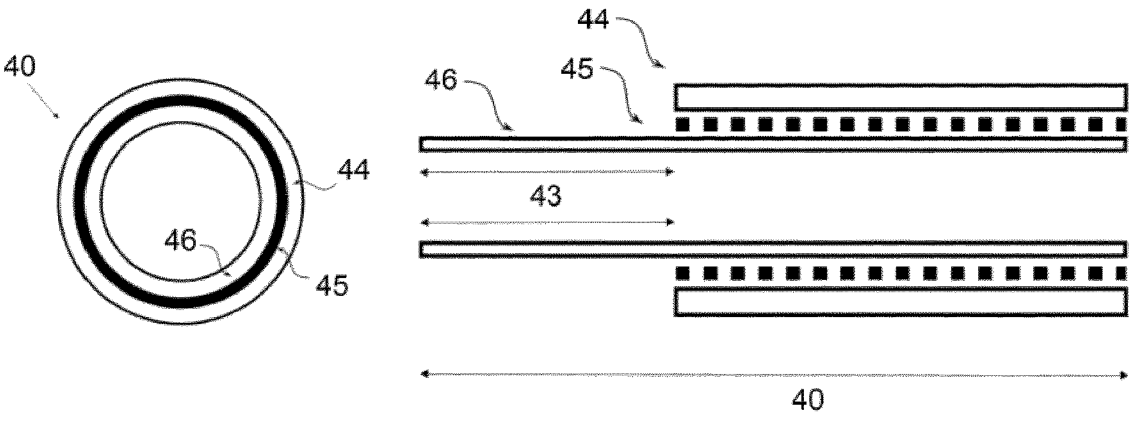
FIGS. 7A-7D schematically illustrate a longitudinal cross-sectional view of the vascular catheter shaft, the tool and the attachment included in the proposed intravascular device of FIGS. 6A-6D.
Figure 7B:
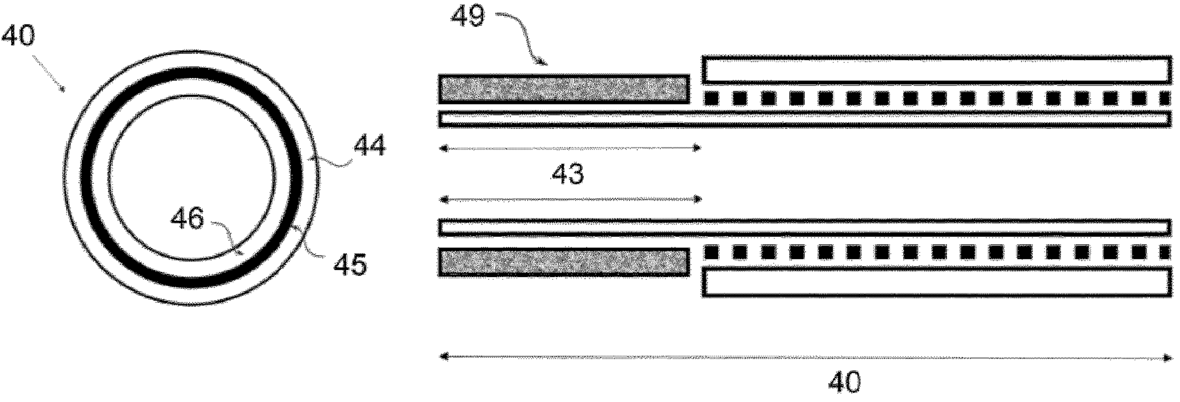
Figure 7C:
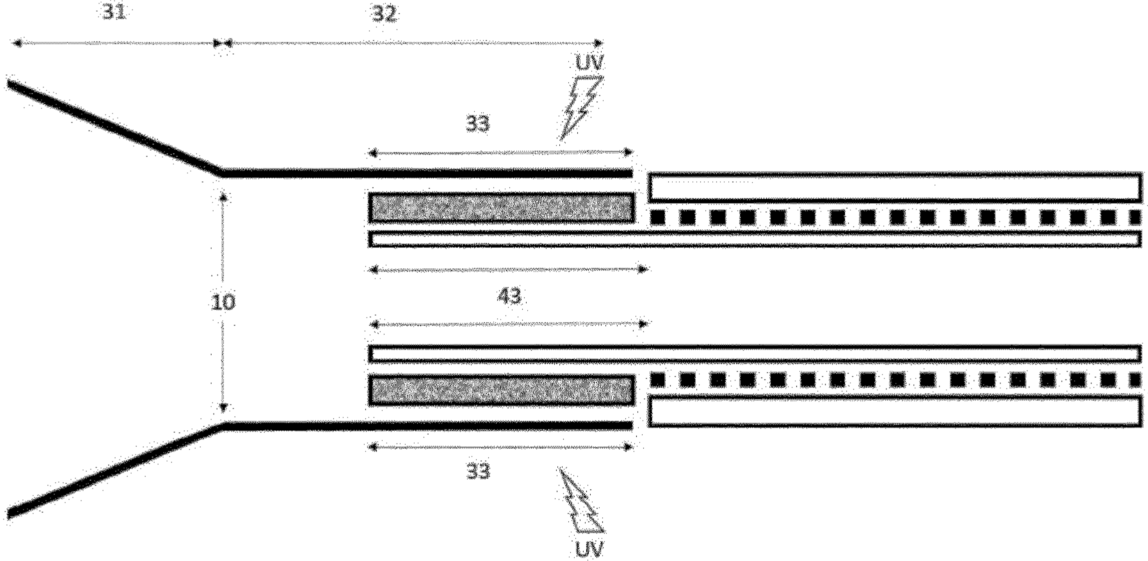
Figure 7D:
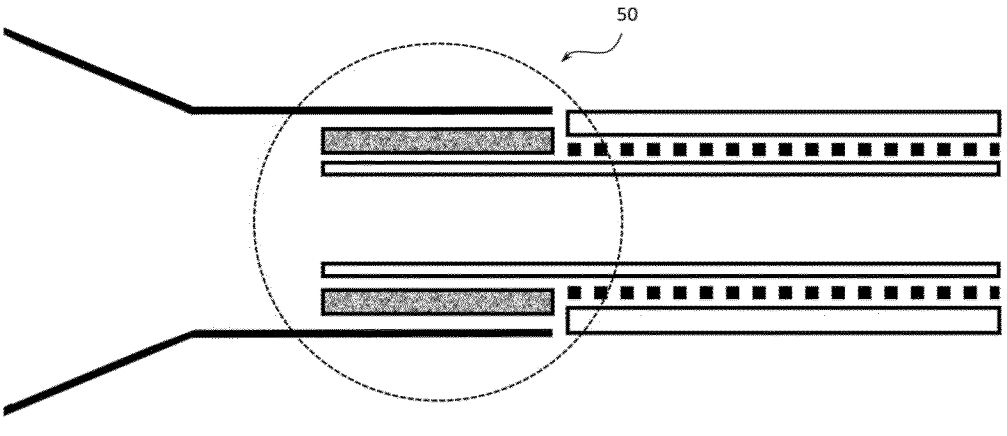

Then the tool's proximal connection portion 33 is placed around the inner jacket 47 (see FIGS. 2D and 3D), and an outer thermoplastic material or outer jacket 48, made of, but not limited to, PEBAX® with shore 25, 35, 40, 55, 63 or 72D, is placed around the tool's proximal connection portion 33 (see FIGS. 2E and 3E). Heat shrinking is then applied (see FIGS. 2F and 3F) to fuse the outer jacket 48 and the inner jacket 47 with the tool's proximal connection portion 33, thereby creating the attachment 50 (see FIGS. 2G and 3G). Accordingly, the thermoplastic material (inner jacket 47 and outer jacket 48) is disposed and extends between and/or over the proximal connection portion 33 of the tool 10 and the distal connection portion 43 of the vascular catheter 40.

The resulting attachment 50 has an outer diameter substantially the same as the vascular catheter outer diameter due to, e.g., the cited heat shrinking. In addition, the disposal of the proximal end of the tool's proximal connection portion 33 against the distal end of the braided layer 45 and the fact that the junction is covered with the inner and outer jackets 47 and 48, minimize kinking of the intravascular device 1 at the distal end of the vascular catheter 40 or at the proximal end of the tool 10 during advancement through the vasculature.

FIGS. 4A-4E and 5A-5E illustrate another embodiment of the intravascular device 1. In this embodiment, the vascular catheter 40 is similar to the vascular catheter 40 of the previous embodiments. That is, the vascular catheter 40 (see FIGS. 4A and 5A) has an inner liner 46 made of e.g., PTFE, surrounded by a braided layer 45 made of e.g., stainless steel, which is itself surrounded by a PEBAX® catheter jacket 44. Glue 49, or any similar adhesive material, is then applied around the portion of the inner liner 46 extending distally beyond the braided layer 45 (see FIG. 4B). The tool's proximal connection portion 33 is placed around the glue 49 (see FIG. 4C and FIG. 5C). Then, UV light is applied to activate glue 49 to bond the tool's proximal connection portion 33 to the inner liner 46 (see FIGS. 4D and 5D), thereby creating an attachment 50 between the vascular catheter's distal connection portion 43 and the tool's proximal connection portion 33 (see FIGS. 4E and 5E). Same as before, the resulting attachment 50 has an outer diameter substantially the same as, or less than, the vascular catheter outer diameter.

In another embodiment, glue 49 can be applied around the inner liner 46 and the braided layer 45, both extending distally beyond the catheter jacket 44 (not shown).

In the embodiments of FIGS. 4A-4E and 5A-5E the braided layer 45 extends beyond the catheter jacket 44. Alternatively, in other embodiments, see FIGS. 6A-6D and 7A-7D, the braided layer 45 does not extend beyond the catheter jacket 44. This is possible since glue 49 can be applied solely over the inner liner 46 (see FIGS. 4B and 5B), and/or over the portion of the braided layer 45 extending distally beyond the catheter jacket 44 (not shown).

In yet another embodiment of the intravascular device 1 (not shown) different to the embodiment of FIGS. 4A-4E, 5A-5E, 6A-6D and 7A-7D, before applying the glue 49, a PEBAX® inner jacket 47 can be placed over (or around) a portion of the inner liner 46 and/or the distal end of the braided layer 45 extending distally beyond the catheter jacket 44, and heat is applied to allow the PEBAX® material to flow into the openings (or cells) of the braided layer 45 and onto the inner liner 46 (see e.g., FIG. 2C and FIG. 3C). It should be noted that the braided layer 45 can distally extend beyond the catheter jacket 44 or not. Moreover, in some embodiments, not illustrated either, an outer jacket 48 can be included after applying the glue 49.

In any of the above-described embodiments, the tool's proximal connection portion 33 can include openings or cells. Additionally, the braided layer 45 can likewise include openings. Thus, the inner and outer jackets 47 and 48 can extend through these openings.

Figure 8:
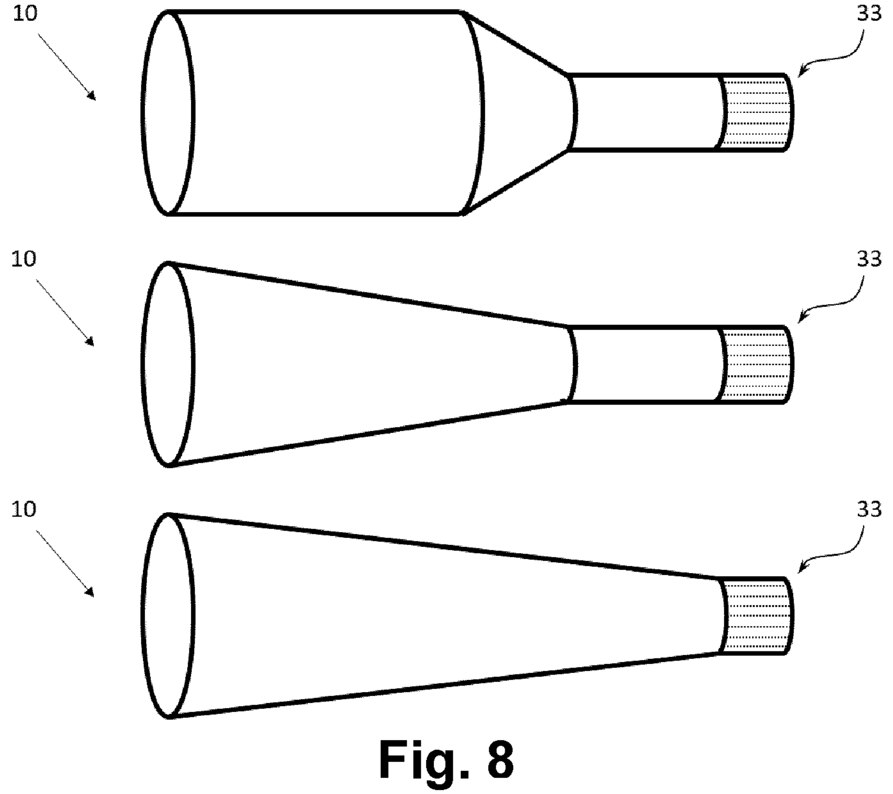
FIG. 8 illustrate different embodiments of the intravascular device tool.

FIG. 8 illustrates different shapes the tool 10, including the proximal connection portion 33, can adopt. Likewise, the tool 10 can be manufactured in different sizes.

In some embodiments, the tool 10 can include a coating. In an embodiment, the coating does not extend over the proximal connection portion 33. In another embodiment, the coating extends over a part of the proximal connection portion 33 or fully covers the proximal connection portion 33. The coating can be non-permeable and/or include an elastomeric or thermoplastic elastomer material such as polyurethane or silicone, among others.

Figure 9:
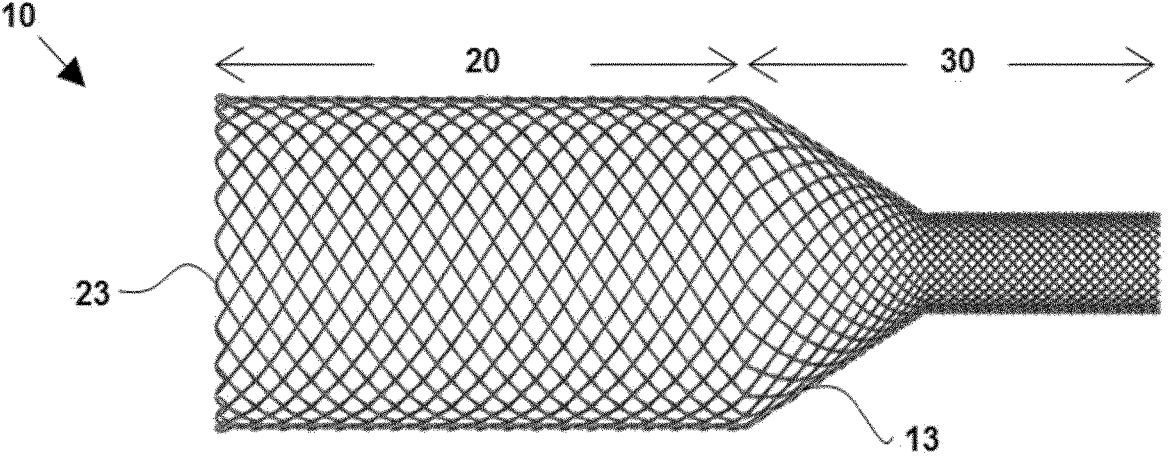
FIG. 9 illustrates a funnel-shaped tool to restore blood flow or remove thrombus, according to a particular embodiment.

With reference to FIG. 9, therein a particular embodiment of the tool 10 is illustrated. The tool 10, which is similar to the one described in WO2020079082, of the same applicant of present invention, is self-expandable and comprises a mesh 13 having two sets of filaments (or wires), equals or different, turning respectively in opposite directions and being intertwined. The filaments can be made of a metal (including metal alloys), polymers, a composite including nitinol or nitinol/platinum, or also DFT® (Drawn Filled Tube), among other materials having suitable mechanical properties. As indicated before, the tool 10 comprises two distinct tubular sections: a second tubular section 20 and a first tubular section 30. The end portion of the second tubular section 20 comprises closed loops 23 configured to act as a spring and providing a smooth distal end to reduce possible vessel damage and improve navigability of the device within the blood vessel.

Figure 10:
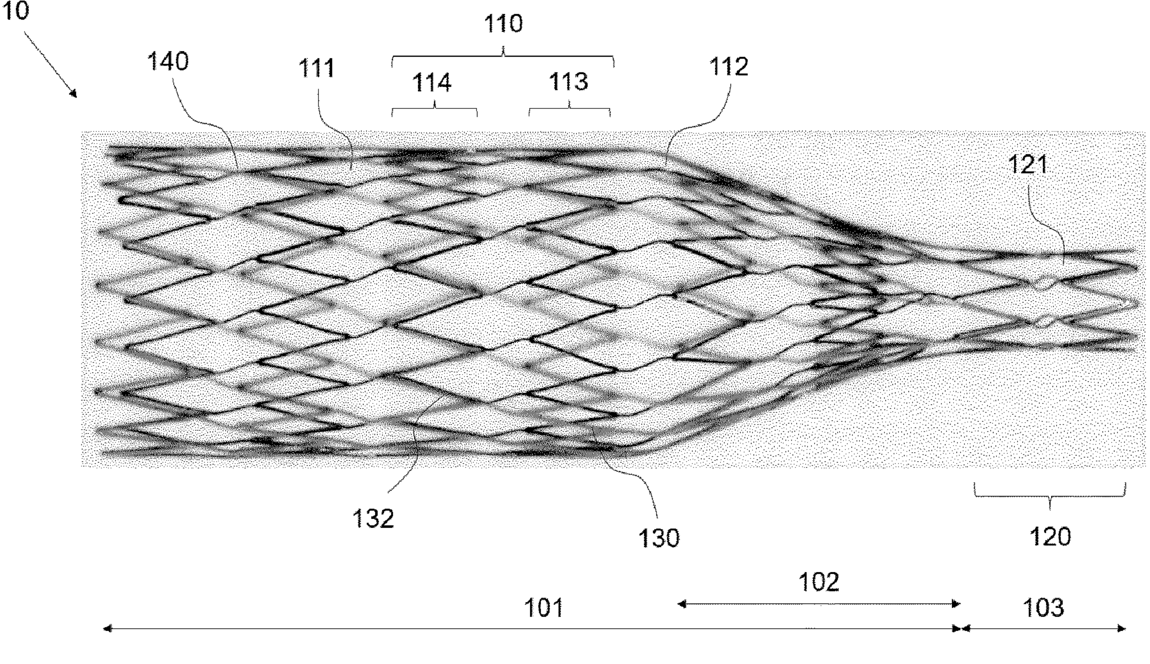
FIG. 10 illustrates a funnel-shaped tool to restore blood flow or remove thrombus, according to a particular embodiment.

Regarding FIG. 10, therein another particular embodiment of the tool 10 is illustrated. The tool 10 has a working portion 101 and a connection portion 103 that extends proximally from a proximal end of the working portion 101 and that can be connected to a pusher, for example a vascular catheter 40, extending proximally from the connection portion. Particularly, the connection portion 103 includes the proximal connection portion 33. The connection portion 103 can be understood as the first sub section 32 (or part thereof) of the other described embodiments. The working portion 101 can be understood as the second tubular section 20 and second sub section 31 of the other described embodiments.

The working portion 101 of this particular embodiment is arranged and configured to provide an outward radial force at every diameter between and including a diameter of a compressed configuration of the working portion 101 and a diameter of an expanded configuration of the working portion 101. The working portion 101 comprises a plurality of crowns 110 of cells 111 that form a tubular-shaped section forming a cylindrically closed structure. The connection portion 103, particularly, also has a tubular-shaped section forming a cylindrically closed structure. The connection portion 103 comprises at least one crown 120 of cells 121, where each cell 121 has an open area bordered by two proximal cell struts, two distal cell struts, and two middle cell struts. Each of the cells 111 of the working portion 101 has an open area bordered by two proximal cell struts 130 (disposed in a proximal cell strut ring 113) two distal cell struts 132 (disposed in a distal cell strut ring 114) and two middle cell struts 112. Each middle cell strut 112 in each crown border two adjacent cells 111 in that crown, and is adapted and configured to be more flexible than the distal cell strut 132 and proximal cell strut 130 to which it extends.

To achieve said flexibility, in some embodiments, the middle cell struts 112 bordering each cell 111 can have a width less than a width of the distal cell struts 132 bordering that cell 111 and less than a width of the proximal cell struts 130 bordering that cell 111. The middle cell struts 112 are configured to provide flexibility by means of one or two hinge portion 140, that is/are arranged/disposed between the proximal and the distal ends of the middle cell strut 112. Each hinge portion can comprise one or two bends.

In the embodiment of FIG. 10, the working portion 101 also includes a tapered portion 102 at the proximal end thereof. The tapered portion 102, which can be understood as the second sub section 31, comprises a plurality of tapered portion struts and has an expanded diameter at a proximal end that is smaller than an expanded diameter of the working portion 101. In these embodiments, the tapered portion 102 has an expanded configuration that defines a frustoconical shape with a closed structure.

The tool 10 of any of the described embodiments can adapt at least its shape and length to a surrounding blood vessel from a retracted position in a compressed state, particularly inside a carrier (e.g., a delivery catheter) to an extended and expanded position, to be appositioned against the inner wall of a blood vessel to receive and retain a thrombus.

The tool 10 can be made of a metal, a metal alloy or a composite including Nitinol or Nitinol/Platinum. However, other types of metals or even other types of materials can be also used, for example cobalt-chromium alloys or iron alloys such as stainless steel or spring steel; also, other materials with shape memory properties can be used, for example cooper or magnesium alloys.

Figure 11:
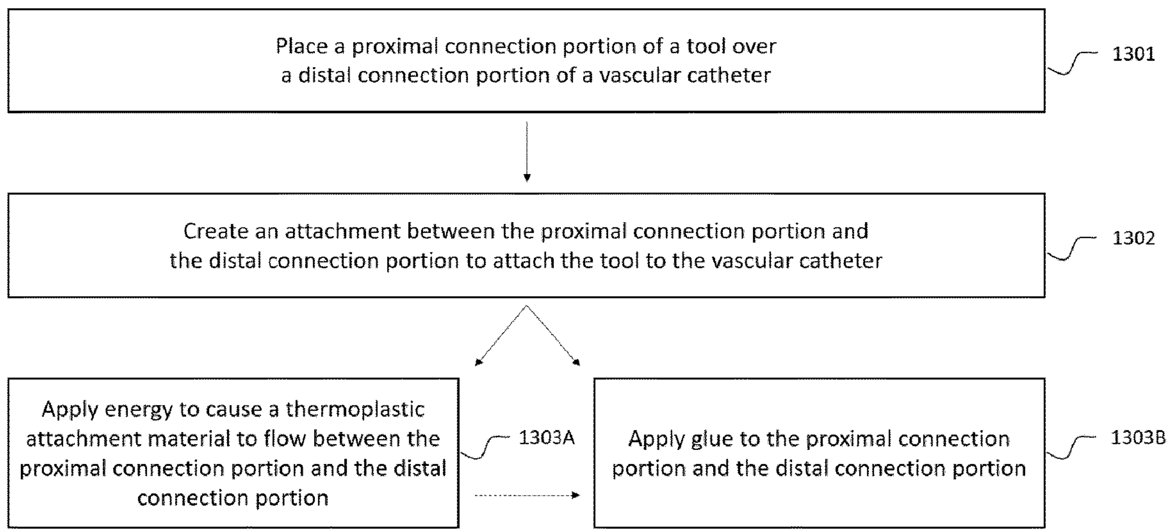
FIG. 11 is a flow chart illustrating a method for attaching a tool to a distal end of a vascular catheter, according to an embodiment of the present invention.

With reference to FIG. 11, therein an embodiment of the proposed method for attaching a tool to a distal end of a vascular catheter is shown. At step 1301 the method comprises placing a proximal connection portion of the tool over a distal connection portion of the vascular catheter. At step 1302, the method comprises creating an attachment between the proximal connection portion and the distal connection portion to attach the tool to the vascular catheter. Then, at step 1303A, energy is applied to cause a thermoplastic material to flow between the proximal connection portion and the distal connection portion. Alternatively, or successively, at step 1303B, glue is applied to the proximal connection portion and the distal connection portion.

Figure 12:
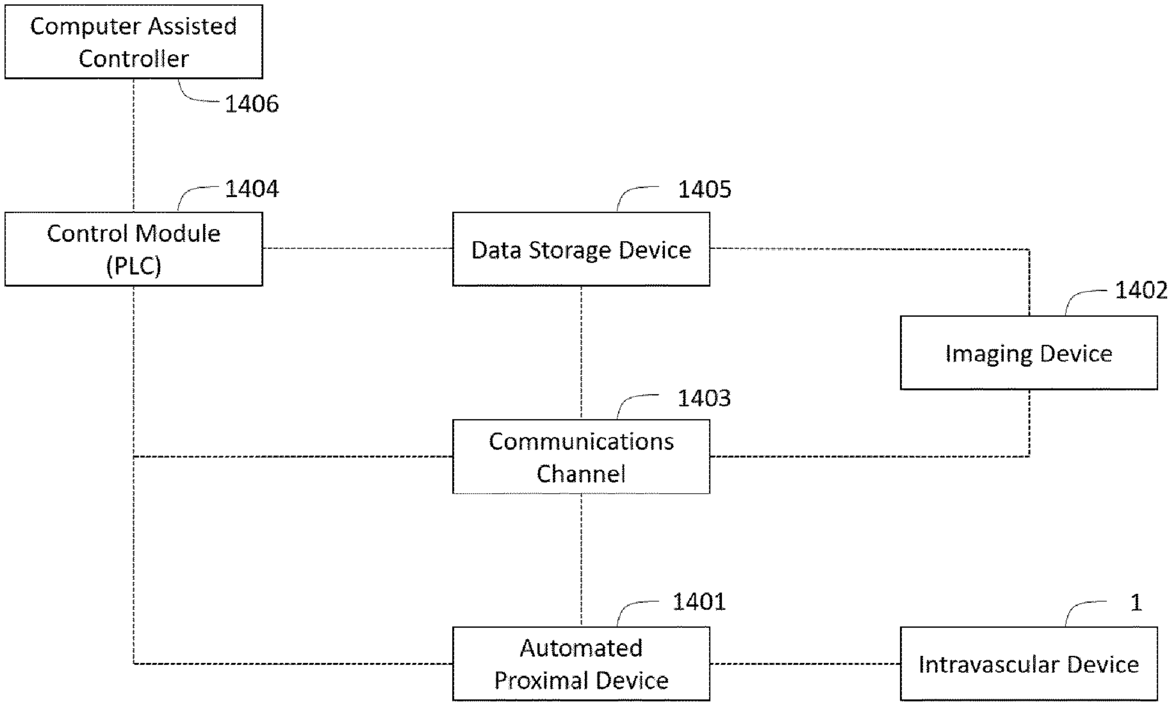
FIG. 12 is a diagram illustrating different elements used for automatically maneuvering the proposed intravascular device, according to an embodiment.

FIG. 12 depicts an example of the intravascular device 1 of the present invention which allows for the automated maneuvering thereof through a vascular system.

According to this particular embodiment, an automated proximal device 1401 provides a guidance system to deploy the intravascular device 1. Moreover, an imaging device 1402 can detect radiopaque markers placed in the tool or in other elements of the intravascular device 1 and generate images. A communications channel 1403 can be used to provide means to transport the images to a control module 1404. The control module 1404 is programmed or configured to allow for guidance of the deployment of the intravascular device 1 and for storage of data on a data storage device 1405. The control module 1404 may be a programmable logic controller, a computer, or the like. In this particular embodiment the control module 1404 is guided by a computer assisted controller 1406. The communications channel 1403 can be Ethernet, Wi-Fi, Bluetooth, or the like. The control module 1404 is programmed to guide a physician or technician operating the intravascular device 1 which allows for the intravascular device 1 to be used in non-hospital settings such as nursing homes or assisted care living facilities.

By using the intravascular device 1, the time required to perform the intravascular intervention is greatly reduced, significantly improving patient outcomes. The control may be also via a controller such as those in use in other current medical devices. In another embodiment, the system may be controlled manually.

Figure 13:
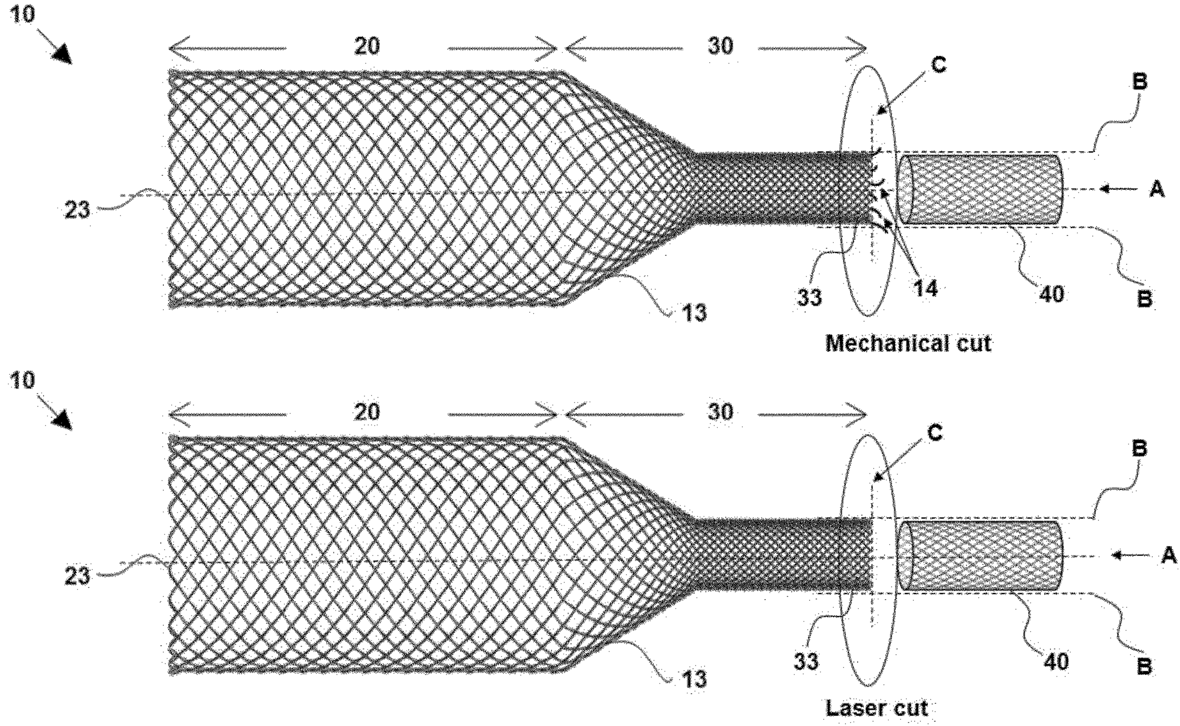
FIG. 13 are two views of the proposed intravascular device showing the difference between the proximal ends being mechanically (top view) or laser-cut (bottom view). In the figure, the axial axis A of the tool, a cylindrical boundary B that is concentric to the axial axis A, and a cross-sectional plane C, are shown.

With reference to FIG. 13 therein two different tools 10, one in which the proximal ends of the proximal connection portion 33 are mechanically cut (top view) and another one in which the proximal ends are laser-cut (bottom view), are shown.

In this regard, a particular embodiment of the invention refers to an intravascular device 1 comprising the cited tool 10 that is adapted to be maneuvered/manipulated during a medical intervention via the vascular device 40 (in this particular case a vascular pusher). Similar to the embodiments explained above, the vascular pusher 40 comprises a distal connection portion 43 and the tool 10 comprises a mesh formed by filaments (as those explained above) and comprises the proximal connection portion 33 having laser-cut proximal ends. In order to keep the tool 10 connected to the vascular pusher 40 the cited attachment 50 is provided between the proximal connection portion 33 and the distal connection portion 43.

Advantageously, thanks to the laser-cut proximal ends, the proximal connection portion 33 is atraumatic. Likewise, since the filaments of the proximal connection portion 33 are cut using a laser-cut technique or laser device the filament ends of the proximal connection portion 33 are smoothed, comprise a perpendicular cross-section with regard to the axial axis A of the tool 10, and are not flared and/or distorted. On the contrary, as can be seen in the top view of FIG. 13, due to the mechanical cut, the filament ends 14 are flared and distorted, i.e., they have an outwardly or inwardly end disposition, are not disposed within the cylindrical boundaries defined by B and do not terminate in the same cross-sectional plane C. Moreover, due to the atraumatic ends, the cited attachment to connect the tool 10 and the vascular pusher 40 is safer and avoids mechanical connection problems such as separation, elongation, or traumatic elements.

Following, different examples of the performance of the proposed intravascular device 1 are detailed. The examples and drawings are provided herein for illustrative purposes, and without intending to be limiting to the present invention.

Example 1: Tensile Resistance Test of the Attachment Between a Catheter Device and a Tool of an Intravascular Device The purpose of this experimental test was to measure the tensile resistance force of the attachment 50 between the catheter device 40 and the tool 10 of the intravascular device 1 of the present invention.

The standard requirements of ISO_10555-1 ask for a measure of tensile force in each junction between tubular portions of an intravascular catheter. A tensile force is applied to each tested piece until the tubular structure breaks or until a junction separates. The following table defines the minimum peak tensile force required for each the diameter of the tubular portion:

TABLE 1

Minimum peak tensile force required in a junction of a device with a tubular portion depending on its outer diameter.

| Smallest outside diameter of the tubular portion of test piece (mm) | Minimum peak tensile force (N) |
|---|---|
| ≥0.55 < 0.75 | 3 |
| ≥0.75 < 1.15 | 5 |
| ≥1.15 < 1.85 | 10 |
| ≥1.85 | 15 |

Accordingly, a peak tensile force of 15 N will fulfill the requirements for any device, considering that the minimum force required for large diameters is 15 N.

Methods

The materials and equipment used during the procedure are exposed in Table 2.

TABLE 2

Tools, equipment, and materials used in Example 1.

| Materials & Equipment | Description |
|---|---|
| Vertical tensile tester | Equipment to perform the peak tensile force measurement |
| Catheter shaft | Shaft of the intravascular catheter device |
| Braided tool | Braided tool with tubular shape intended to be connected to the catheter shaft to form the intravascular device |
| Polyamide tube | Tube of polyether bloc amide thermoplastic elastomers (PEBAX ®) |
| Loctite adhesive | Cyanoacrylate adhesives (Loctite ®) |

Different attachment materials were used to assemble the catheter shaft and the tool:

- Reflow techniques using thermoplastic materials (i.e., PEBAX®): seven trials with uncoated tools (trial 1 to 7) and ten trials with coated tools (trial 8 to 17).
- Gluing techniques (i.e., Loctite® adhesive): four trials with uncoated tools.

Tensile measurement: The peak tensile force of the connection between the catheter shaft and braided tool was measured until breakage of the material of the shaft or tool or until detachment of the attachment between the tool and the catheter shaft. The tensile force was then recorded.

Results and Conclusion

Table 3 shows the results of attachment tensile force by both techniques:

TABLE 3

Attachment tensile force. Failure modes: Material = the shaft brakes (e.g., inner liner), Attachment = the tool detaches from the shaft.

| Sample | Failure Mode | Tensile Force [N] | Average [N] |
|---|---|---|---|
| Reflow trial 1 | Material | 17.9 | 17.53 |
| Reflow trial 2 | Material | 18.0 | |
| Reflow trial 3 | Material | 18.1 | |
| Reflow trial 4 | Material | 17.4 | |
| Reflow trial 5 | Material | 17.5 | |
| Reflow trial 6 | Material | 17.8 | |
| Reflow trial 7 | Material | 16.0 | |
| Reflow trial 8 | Material | 21.7 | 22.31 |
| Reflow trial 9 | Material | 22 | |
| Reflow trial 10 | Material | 22.9 | |
| Reflow trial 11 | Material | 21.9 | |
| Reflow trial 12 | Material | 23.3 | |
| Reflow trial 13 | Material | 16.9 | |
| Reflow trial 14 | Material | 23.6 | |
| Reflow trial 15 | Material | 24.7 | |
| Reflow trial 16 | Material | 22.2 | |
| Reflow trial 17 | Material | 23.9 | |
| Glue trial 1 | Material | 18.8 | 17.88 |
| Glue trial 2 | Material | 17.4 | |
| Glue trial 3 | Attachment | 17.2 | |
| Glue trial 4 | Material | 18.1 | |

The results showed a tensile force higher than 15 N for all trials/samples including the reflow technique (with coated or uncoated tools) and the glue technique trials. Consequently, all the obtained values are greater than the minimum tensile force required by the standard requirements for use of intravascular catheters.

These results are related with the safety of the intravascular device 1 during the clinical use, therefore, high values of tensile strength inhibit the possibilities of a premature breakage of the attachment/connection due to an excessive tension during retrieval or navigation.

In conclusion, the tested technology meets the requirements and consequently is able to be advanced, pulled and kept intact within the blood vessel during the intervention.

Example 2: Flexibility Testing of the Distal Portion of an Intravascular Device Including an Attachment Between a Catheter Device and a Tool The anatomy of the brain presents very irregular pathways where intravascular catheters should navigate through to withdrawn thrombus from a target brain location. Intravascular devices must be configured to undergo torque and tensile movements. Therefore, the elements and junctions of the elements of those intravascular devices must present a desired flexibility and strength to avoid kinking and detachment.

The purpose of this experimental test was to determine if the intravascular device 1 of the present invention is configured to be advanced through neurovasculature in terms of the flexibility of its attachment section between the tool 10 and the catheter shaft 40 thereof.

The evaluation of the flexibility was quantified using a 2-point bending (2PB) method to provide quantitative insight into the final behavior regarding the navigability, trackability and pushability of the intravascular device 1.

The intravascular device 1 should present a proper flexibility to navigate through tortuous paths but also to generate a good pushability by means of the distally directed force transmitted from the proximal portion (i.e., catheter shaft 40) to the distal portion (i.e., tool 10) of the device.

A high flexibility will improve the navigability but may decrease the pushability, a low flexibility will improve the pushability but may decrease the navigability. Therefore, a proper flexibility has to be selected to accept or reject the device configuration.

Methods

To quantify the proper flexibility to be considered for the device development, a load is applied to the selected zone (e.g., in this case in the attachment 50 or junction zone), in the vertical direction, to generate a predefined displacement (1.5 mm of travel) of the distal tip (including the tool 10) of the device. If the load is inside the predefined range, the structural configuration of the device is accepted, since the device will reach the required navigability and pushability (e.g., in terms of selected flexibility of its elements).

The selected load should be inside the range [0.05-0.2 N]. The highest value is set according to the load applied to a device which navigates not entirely as it is intended, and the lowest value is set according to the load applied to a device which cannot transmit the proper distally directed force and therefore do not pushes as required. If the load applied to a sample is inside the range, therefore the tested device meets the navigability and pushability requirements due to the proper flexibility of its structural configuration.

The 2PB evaluation was performed in 10 samples with two different outer jacket 44 materials: Configuration A: 5 samples with value of shore of 40D (less flexible), samples 1 to 5; and Configuration B: 5 samples with a value of shore of 35D (more flexible), samples 6 to 10. The testing point was set in the junction/attachment 50 of the intravascular device 1. The load was applied in the testing point, in the vertical direction, until the distal tip reaches a displacement of 1.5 mm.

The 2PB apparatus (e.g., vertical tensile tester) consists of a shaft holding fixture and a calibrated load cell (of 50 N) which includes a tip plunger fixture located 1.5 cm from the shaft holding fixture. The apparatus is configured to apply and accurately measure loads and deflections (i.e., displacement) to the sample mounted in a 2PB bending fixture. The catheters were put over the shaft holding fixture and the catheter testing point was located in the plunger fixture location. The plunger applied a load by means of the load cell until the distal end of the device reaches a displacement of 1.5 mm from the vertical starting position (i.e., 0° from the horizontal axis), then, the maximum force was recorded, as showed in Table 4. This testing method is according to the standard ASTM D790-17 regarding Test Methods for Flexural Properties, which is similar to the standard ASTM F2606-08 (2021) regarding Standard Guide for Three-Point Bending.

Results and Conclusion

TABLE 4

Load (N) required, and applied by the calibrated load cell to the intravascular device testing point, to reach a displacement of 1.5 mm by the distal tip of the samples.

| Sample | Configuration | Load (N) | Average Load (N) |
|---|---|---|---|
| 1 | A | 0.142 | 0.134 |
| 2 | A | 0.130 | |
| 3 | A | 0.123 | |
| 4 | A | 0.134 | |
| 5 | A | 0.140 | |
| 6 | B | 0.0618 | 0.0671 |
| 7 | B | 0.0829 | |
| 8 | B | 0.0608 | |
| 9 | B | 0.0538 | |
| 10 | B | 0.0763 | |

2PB test showed that all the recorded load values were inscribed inside the predefined inclusion criteria range of 0.5-2.0 N, regarding the applied vertical load. Therefore, all the tested samples and their configurations (both, A and B), in terms of the average values, present proper structural properties, by means of the flexibility of its structure and materials, consequently, all the devices are configured to achieve good navigability and pushability.

In conclusion, the samples of the intravascular device 1 of the present invention are configured to undergo torque and tensile movements when navigating through the intravascular vessels. Therefore, the elements and junctions of those intravascular devices present a desired flexibility and strength to avoid kinking and detachment and are configured to transmit a proper pushability when navigating.

Unless otherwise indicated, all numbers expressing measurements, conditions, and so forth used in the specification and claims are to be understood as being modified in all instances by the term “about”. Accordingly, unless indicated to the contrary, the numerical parameters set forth in this specification and attached claims are approximations that can vary depending upon the desired properties sought to be obtained by the presently disclosed subject matter. Throughout the description and claims the word “comprise” and its variations such as “comprising” are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein.

The present disclosure and/or some other examples have been described in the above. According to descriptions above, various alterations may be achieved. All applications, modifications and alterations required to be protected in the claims may be within the protection scope of the present disclosure.

The scope of the present invention is defined in the following set of claims.

The invention claimed is:

1. An intravascular device, comprising:

a vascular pusher comprising a distal connection portion;

a tool attached to, and extending from, the distal connection portion of the vascular pusher, the tool being formed by a mesh of at least two sets of filaments, and comprising a proximal connection portion including laser-cut proximal ends of the at least two sets of filaments; and an attachment between the proximal connection portion of the tool and the distal connection portion of the vascular pusher, the attachment being adapted to keep the tool connected to the vascular pusher and having an outer diameter substantially equal to an outer diameter of the vascular pusher.

2. The device of claim 1, wherein the laser-cut proximal ends of the at least two sets of filaments are disposed within a same cylindrical boundary, without extending outwardly or inwardly.

3. The device of claim 1, wherein the laser-cut proximal ends comprise perpendicular cross-sections with regard to an axial axis of the tool.

4. The device of claim 1, wherein the laser-cut proximal ends terminate in a same cross-sectional plane.

5. The device of claim 1, wherein the attachment comprises a thermoplastic material extending between or over the proximal connection portion of the tool and the distal connection portion of the vascular pusher.

6. The device of claim 1, wherein the attachment comprises glue extending between or over the proximal connection portion of the tool and the distal connection portion of the vascular pusher.

7. The device of claim 1, wherein the mesh comprises at least two distinct tubular sections, a first tubular section of uniform diameter and a second tubular section comprising a shape with a progressive reduction of diameter to open and create a space for a thrombus, the first tubular section including the proximal connection portion of the tool.

8. The device of claim 1, wherein the vascular pusher comprises a hypotube, a vascular catheter or a tubular element.

9. The device of claim 8, wherein the mesh further comprises a third tubular section of uniform diameter.

10. A method of manufacturing an intravascular device, comprising:

providing a vascular pusher comprising a distal connection portion;

attaching a tool to the vascular pusher, extending from the distal connection portion of the vascular pusher, the tool being formed by a mesh of at least two sets of filaments, and comprising a proximal connection portion including laser-cut proximal ends of the at least two sets of filaments; and providing an attachment between the proximal connection portion of the tool and the distal connection portion of the vascular pusher to keep the tool connected to the vascular pusher, the attachment having an outer diameter substantially equal to an outer diameter of the vascular pusher.

11. The method of claim 10, wherein the laser-cut proximal ends being cut by means of a laser-cut technique.

12. The method of claim 10, wherein the laser-cut proximal ends being cut by means of a laser device.

13. The method of claim 10, wherein the laser-cut proximal ends of the at least two sets of filaments are disposed within a same cylindrical boundary, without extending outwardly or inwardly.

14. The method of claim 10, wherein the laser-cut proximal ends comprise perpendicular cross-sections with regard to an axial axis of the tool.

15. The method of claim 10, wherein the laser-cut proximal ends terminate in a same cross-sectional plane.

* * * * *